US011806386B2

(12) United States Patent
Thomas et al.

(10) Patent No.: US 11,806,386 B2
(45) Date of Patent: Nov. 7, 2023

(54) TYPE I DIABETES THERAPY

(71) Applicant: St. Vincent's Institute of Medical Research, Fitzroy (AU)

(72) Inventors: Helen E. Thomas, Fitzroy (AU); Thomas W. H. Kay, Fitzroy (AU); Balasubramanian Krishnamurthy, Fitzroy (AU); Gaurang Jhala, Fitzroy (AU)

(73) Assignee: St. Vincent's Institute of Medical Research, Fitzroy (AU)

( * ) Notice: Subject to any disclaimer, the term of this patent is extended or adjusted under 35 U.S.C. 154(b) by 643 days.

(21) Appl. No.: 16/637,304

(22) PCT Filed: Aug. 7, 2018

(86) PCT No.: PCT/AU2018/050823
§ 371 (c)(1),
(2) Date: Feb. 7, 2020

(87) PCT Pub. No.: WO2019/028503
PCT Pub. Date: Feb. 14, 2019

(65) Prior Publication Data
US 2020/0345815 A1 Nov. 5, 2020

(30) Foreign Application Priority Data
Aug. 7, 2017 (AU) .............................. 2017903125

(51) Int. Cl.
| | |
|---|---|
| *A61K 38/28* | (2006.01) |
| *A61P 3/10* | (2006.01) |
| *A61K 31/437* | (2006.01) |
| *A61K 31/4985* | (2006.01) |
| *A61K 31/519* | (2006.01) |
| *A61K 31/529* | (2006.01) |
| *A61K 31/5355* | (2006.01) |
| *A61K 31/541* | (2006.01) |
| *A61K 31/553* | (2006.01) |
| *A61K 38/17* | (2006.01) |
| *A61K 38/46* | (2006.01) |
| *A61K 38/51* | (2006.01) |

(52) U.S. Cl.
CPC ............ *A61K 38/28* (2013.01); *A61K 31/437* (2013.01); *A61K 31/4985* (2013.01); *A61K 31/519* (2013.01); *A61K 31/529* (2013.01); *A61K 31/5355* (2013.01); *A61K 31/541* (2013.01); *A61K 31/553* (2013.01); *A61K 38/1709* (2013.01); *A61K 38/465* (2013.01); *A61K 38/51* (2013.01); *A61P 3/10* (2018.01)

(58) Field of Classification Search
None
See application file for complete search history.

(56) References Cited

U.S. PATENT DOCUMENTS 8,153,121 B2    4/2012 Smith et al.

FOREIGN PATENT DOCUMENTS

| EP | 1626083 A1 | 2/2006 |
| WO | WO 2005/076965 A2 | 8/2005 |
| WO | WO 2011/091138 A1 | 7/2011 |

OTHER PUBLICATIONS

Staeva et al, Diabetes, vol. 62, pp. 9-17, Jan. (Year: 2013).*
Bresson et al, The Journal of Clinicla Investigation, vol. 116, No. 5, pp. 1371-1381, May (Year: 2006).*
Brosius et al, Diabetologia, vol. 16, No. 59, pp. 1624-1627, Jun. (Year: 2016).*
Hirsch et al., Antigen-based immunotherapy for autoimmune disease: current status. Immunotargets Ther. 2014;4:1-11. Published Dec. 16, 2014. doi: 10.2147/ITT.S49656.
Jhala et al., Perinatal tolerance to proinsulin is sufficient to prevent autoimmune diabetes. JCI Insight. Jul. 7, 2016; 1(10): e86065. Published online Jul. 7, 2016. doi: 10.1172/jci.insight.86065.
Takiishi et al., Reversal of autoimmune diabetes by restoration of antigen-specific tolerance using genetically modified Lactococcus lactis in mice. J Clin Invest. 2012;122(5):1717-1725. doi:10.1172/JCI60530.
International Search Report and Written Opinion for Application No. PCT/AU2018/050823, dated Aug. 30, 2018.
Trivedi et al., Repurposed JAK1/JAK2 Inhibitor Reverses Established Autoimmune Insulitis in NOD Mice. Diabetes. Jun. 2017;66(6):1650-1660. doi: 10.2337/db16-1250. Epub Mar. 14, 2017.
International Preliminary Report on Patentability for Application No. PCT/AU2018/050823, dated Feb. 20, 2020.
PCT/AU2018/050823, Feb. 20, 2020, International Preliminary Report on Patentability.
PCT/AU2018/050823, Aug. 30, 2018, International Search Report and Written Opinion.

* cited by examiner

*Primary Examiner* — Zinna Northington Davis
(74) *Attorney, Agent, or Firm* — Wolf, Greenfield & Sacks, P.C.

(57) ABSTRACT

The present invention relates to novel methods and therapies for treating, preventing or delaying the onset of type 1 diabetes. In one aspect, the invention provides a method of preventing, delaying the onset of, or delaying the progression of, type 1 diabetes (T1D) in an individual, the method comprising providing in the individual an anti-inflammatory compound; and a pancreatic autoantigen or a derivative or variant thereof; thereby preventing, delaying the onset of, or delaying the progression of, T1D in the individual.

11 Claims, 8 Drawing Sheets

Specification includes a Sequence Listing.

TYPE I DIABETES THERAPY

RELATED APPLICATIONS

This application is a national stage filing under 35 U.S.C. § 371 of international application number PCT/AU2018/050823, filed Aug. 7, 2018, which claims the benefit under 35 U.S.C. § 119(e) of the filing date of Australian provisional application number AU 2017903125, filed Aug. 7, 2017, the entire contents of each of which are incorporated by reference herein.

FIELD OF THE INVENTION

The invention relates to novel methods and compositions for treating, delaying the onset of, or preventing or delaying the development of type 1 diabetes in individuals.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Apr. 28, 2020, is named S2113370000US00-SEQ-KZM and is 1 kilobyte in size.

BACKGROUND OF THE INVENTION

Type 1 diabetes (T1D) is an autoimmune disorder that results from the T-cells of the body's immune system attacking the β-cells of the islets of Langerhans in the pancreas. While it represents 5%-10% of all diabetes cases, type 1 diabetes accounts for over 90% of diabetes cases in children.

The main aetiology of type 1 diabetes is a drop in insulin levels due to the destruction of the insulin-producing pancreatic β-cells, which leads to abnormally high blood glucose levels. This can lead to symptoms of the disease such as frequent urination; extreme hunger and thirst; weight loss; fatigue and irritability. However, over time, sustained hyperglycemia leads to a number of other more serious complications such as heart disease, high blood pressure, kidney disease and nervous system disease. It is these complications from diabetes that ultimately lead to death if left untreated.

As an autoimmune disease, self-reactive T cells infiltrate the pancreatic islets, causing inflammation (insulitis) and progressively destroying insulin-producing β-cells. Unfortunately, the pathogenic mechanisms behind the initiation of T1D are poorly understood, and without a cure, it remains one of few diseases where incidence and prevalence continue to rise annually.

There is an increasing role for antigen-specific immunotherapy in diabetes prevention. Autoimmunity develops when immune checkpoints designed to maintain tolerance to self-antigens fail. In NOD mice, there is strong evidence suggesting proinsulin is the essential self-antigen to which tolerance is lost. Induction of tolerance to proinsulin via oral, intranasal and subcutaneous modes of administration ultimately protects NOD mice from T1D, however, these methods require regular dosing to achieve such effect, not dissimilar to current first line insulin therapy in T1D.

There remains a need for the development of new methods and compositions for treating, preventing and/or delaying the onset of type 1 diabetes.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

The present invention provides a method of preventing, delaying the onset of, or delaying the progression of, type 1 diabetes (T1D) in an individual, the method comprising providing in the individual:
an anti-inflammatory compound; and
a pancreatic autoantigen or a derivative or variant thereof;
thereby preventing, delaying the onset of, or delaying the progression of, T1D in the individual.

In any embodiment of the invention, the pancreatic autoantigen is a β-cell autoantigen. Preferably, the autoantigen is a β-cell specific autoantigen.

In any embodiment of the invention, the pancreatic autoantigen is selected from the group consisting of proinsulin, islet-specific glucose-6-phosphatase catalytic subunit related protein (IGRP), glutamate decarboxylase (GAD), islet-antigen 2 (IA-2) and zinc transporter 8 (ZnT8).

In any embodiment of the present invention, preferably the autoantigen is proinsulin.

In any embodiment of the invention, more than one pancreatic autoantigen is provided in the individual.

Preferably, the derivative or variant of the pancreatic autoantigen is a fragment of a pancreatic autoantigen having at least one effector T cell epitope.

In any method of the invention, the individual is at risk of developing T1D. Preferably, the method further comprises the step of determining whether the individual is at risk of developing T1D.

An individual may be considered at risk of developing T1D based on family history or genetic susceptibility. For example, an individual having a high risk HLA genotype may be at risk of developing type 1 diabetes. The individual may have HLA and/or non-HLA risk factor genotypes as described herein. Typically, a high risk genotype includes DRB1*0301-DQB1*0201 (DR3-DQ2) and/or DRB1*0401-DQB1*0302 (DR4-DQ8). The genotype associated with the highest risk for T1D is the heterozygous DR3/4 genotype. Other genotypes that increase the risk of developing T1D are described herein. The individual may be classified as having pre-stage 1 diabetes as described herein.

An individual may be at risk of developing type 1 diabetes if 2 or more autoantibodies against β-cell specific antigens are detectable in the individual. Preferably the antibodies to the β-cell specific antigens are selected from the consisting of Carboxypeptidase H, Chromogranin A, Glutamate decarboxylase (GAD), Imogen-38, Proinsulin/Insulin, Islet antigen-2 and 2β (IA-2), and zinc transporter 8 (ZnT8). Preferably, the 2 or more autoantibodies are to 2 or more of the antigens (pro)insulin, GAD, ZnT8, and IA-2. An individual with autoantibodies against β-cell specific antigens may or may not also have a high risk HLA genotype.

In any method of the invention, the individual may have detectable levels of circulating endogenous insulin.

In any method of the invention, the individual may have dysglycaemia, or abnormal blood glucose levels. Dysglycaemia or abnormal blood glucose levels may be determined by a method described herein.

In any method of the invention, the individual may display at least one symptom of T1D, wherein the symptom may be one or more of: polyuria, polydipsia, weight loss, fatigue, and diabetic ketoacidosis (DKA).

The present invention also provides a method of treating early stage type 1 diabetes (T1D) in an individual,
the method comprising providing in the individual:
an anti-inflammatory compound; and
a pancreatic autoantigen or a derivative or variant thereof;
thereby treating early stage T1D in the individual. Preferably, the pancreatic autoantigen is proinsulin.

Indicators of early stage type 1 diabetes include one or more of: autoimmunity to at least two β-cell specific antigens, dysglycaemia, evidence of β-islet cell loss and reduced endogenous insulin production.

In any method of the invention, the anti-inflammatory compound and pancreatic autoantigen (e.g., proinsulin) or a derivative or variant thereof are provided simultaneously. Alternatively, the anti-inflammatory compound may be provided in the individual prior to the provision of proinsulin or a derivative or variant thereof. In one scenario, provision of the anti-inflammatory compound in the individual commences prior to the autoantigen or a derivative or variant thereof, and continually during the time autoantigen or a derivative or variant thereof is provided. In alternative scenarios, the anti-inflammatory compound is provided in the individual for a shorter period of time than the autoantigen, including for a time sufficient to reduce cytokine production in the individual.

In one embodiment, the anti-inflammatory compound is administered for at least 1 month prior to providing the autoantigen (e.g., proinsulin), derivative or variant thereof.

In an alternative embodiment, the autoantigen or a derivative or variant thereof is provided in the individual for at least 1 month in conjunction with the anti-inflammatory compound.

The present invention provides a method of preventing, delaying the onset of, or delaying the progression of, type 1 diabetes (T1D) in an individual, the method comprising providing in the individual:
an anti-inflammatory compound,
wherein the anti-inflammatory compound is provided in the individual for a period of time sufficient to reduce the level of proinflammatory cytokine-mediated gene expression in the individual; and
a pancreatic autoantigen or a derivative or variant thereof;
thereby preventing, delaying the onset of, or progression of, T1D in the individual.

The present invention also provides a method for prolonging the production of endogenous insulin in an individual at risk of, or showing early symptoms of T1D, the method comprising providing in the individual:
an anti-inflammatory compound; and
a pancreatic autoantigen or a derivative or variant thereof;
thereby prolonging the production of endogenous insulin in the individual.

The present invention also provides a method of preventing or delaying the progression of T1D in an individual, comprising administering to an individual having, or suspected of having early signs of T1D, an anti-inflammatory compound, wherein preferably the anti-inflammatory compound inhibits or reduces the level of proinflammatory cytokine-mediated gene expression. More preferably, the anti-inflammatory compound is a JAK inhibitor.

In any method of the invention, the pancreatic autoantigen (such as proinsulin, IGRP or other pancreatic autoantigen) or a derivative or variant thereof is provided in the individual by administering to the individual (a) a therapeutically effective amount of the pancreatic autoantigen or a derivative or variant thereof, or (b) a pharmaceutical composition comprising a therapeutically effective amount of the pancreatic autoantigen, derivative or variant thereof. The pharmaceutical composition comprising proinsulin, or a derivative or variant thereof may be administered orally, subcutaneously, intravenously, intranasally, by inhalation, intramuscularly or intradermally.

In any embodiment of the present invention, the pancreatic autoantigen, derivative or variant thereof, is provided to the individual by administering to the individual, a genetically modified bacterium that expresses a gene encoding the autoantigen (e.g., proinsulin), derivative or variant thereof. The genetically modified bacterium may express one or more additional genes encoding one or more additional autoantigens.

In still a further embodiment, the autoantigen, derivative or variant thereof may be provided in a dendritic cell, modified to express the autoantigen (e.g., proinsulin) or derivative thereof.

In any method of the invention, the autoantigen (e.g. proinsulin) or a derivative or variant thereof is provided in the individual by administering to the individual, a composition comprising a nucleic acid construct for expressing the pancreatic autoantigen or derivative or variant thereof in the individual. The nucleic acid construct may encode more than one pancreatic autoantigen, for example, a combination of any two or more of proinsulin, islet-specific glucose-6-phosphatase catalytic subunit related protein (IGRP), glutamate decarboxylase (GAD), islet-antigen 2 (IA-2) and zinc transporter 8 (ZnT8).

The present invention also provides compositions, including pharmaceutical compositions, for providing in an individual, an anti-inflammatory compound and/or a pancreatic autoantigen (such as proinsulin) or a derivative or variant thereof. The pharmaceutical compositions are for use in preventing or delaying the onset of type 1 diabetes in an individual, including in an individual at risk of, or showing early signs of type 1 diabetes. Preferably, a composition of the invention further comprises a physiologically or pharmaceutically acceptable carrier, diluent or excipient.

A pharmaceutical composition described herein may be administered orally, subcutaneously, intravenously, intranasally, by inhalation, intramuscularly or intradermally. Further, a pharmaceutical composition described herein may be adapted for oral, subcutaneous, intravenous, intranasal, intramuscular or intradermal administration.

A pharmaceutical composition described herein may comprise a genetically modified bacterium which expresses a pancreatic autoantigen, including proinsulin, or a derivative or variant thereof.

A pharmaceutical composition described herein may comprise a composition comprising a nucleic acid construct for expressing the proinsulin or derivative or variant thereof in an individual.

A pharmaceutical composition, as described herein may include a dendritic cell modified to express proinsulin, or a derivative or variant thereof when administered to an individual.

A pharmaceutical composition, as described herein, may include an anti-inflammatory compound and proinsulin, or a derivative or variant thereof, for use in preventing or delaying the onset of type 1 diabetes in an individual.

In any embodiment of the present invention, the derivative of proinsulin may be insulin. Alternatively, the derivative may be any other fragment of proinsulin wherein the fragment comprises at least one effector T cell epitope.

In any embodiment of the present invention, the anti-inflammatory compound may be an inhibitor of proinflammatory cytokine-regulated gene expression. Preferably, the inhibitor of proinflammatory cytokine-regulated gene expression is a JAK inhibitor. The JAK inhibitor may inhibit JAK1, JAK2 and/or JAK3. The JAK inhibitor may inhibit more than one JAK, for example, it may inhibit both JAK1 and JAK2. Alternatively, the JAK inhibitor may be selective for one subtype of JAK, e.g., JAK1, JAK2 or JAK3.

In any embodiment of the present invention, the JAK inhibitor may be selected from the group consisting of: Ruxolitinib, Tofacitinib, Oclacitinib, Baricitinib, Filgotinib, Gandotinib, Lestaurtinib, Momelotinib, Pacritinib, Upadacitinib, Peficitinib and any other JAK inhibitor as described herein.

In any method of the invention, the JAK inhibitor is provided to the individual by administering to the individual (a) a therapeutically effective amount of the JAK inhibitor, or (b) a pharmaceutical composition comprising a therapeutically effective amount of the JAK inhibitor.

The present invention also provides use of:
an anti-inflammatory compound; and
a pancreatic autoantigen or a derivative or variant thereof;
in the manufacture of a medicament for preventing, delaying the onset of, or delaying progression of, type 1 diabetes in an individual. The pancreatic autoantigen is preferably selected from the group consisting of: proinsulin, islet-specific glucose-6-phosphatase catalytic subunit related protein (IGRP), glutamate decarboxylase (GAD), islet-antigen 2 (IA-2) and zinc transporter 8 (ZnT8). More preferably, the autoantigen is proinsulin.

In further embodiments, the medicament comprises more than one pancreatic autoantigen or derivative or variant thereof.

The present invention also provides for the use of a first and second composition, in the manufacture of a medicament for preventing or delaying the onset of type 1 diabetes in an individual, wherein, the first composition comprises an anti-inflammatory compound and the second composition comprises a pancreatic autoantigen (such as proinsulin), or a derivative or variant thereof.

The first composition may be administered to the individual prior to the administration of the second composition. The first and second compositions may be administered concomitantly. The first composition may be administered to the individual for a period of time, sufficient to reduce proinflammatory cytokine-mediated gene signalling in the individual, prior to administration of the second composition. Preferably, the first composition is administered to the individual for at least one month prior to administration of the second composition. Once administration of the second composition is commenced, the administration of the first composition may be continued or discontinued or modified.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

(A) Study cohorts depicting duration and type of treatment received.

(B) Proinsulin 2 expression calculated relative to β-actin expression in thymic homogenates of WT-NOD and TIP2 mice of various ages (mean±SEM). All TIP2 mice received doxycycline from embryonic day 12 to day 7 post-birth unless specified. TIP2 mice which never received doxycycline expressed proinsulin throughout life (20 weeks of age).

Figure 2:
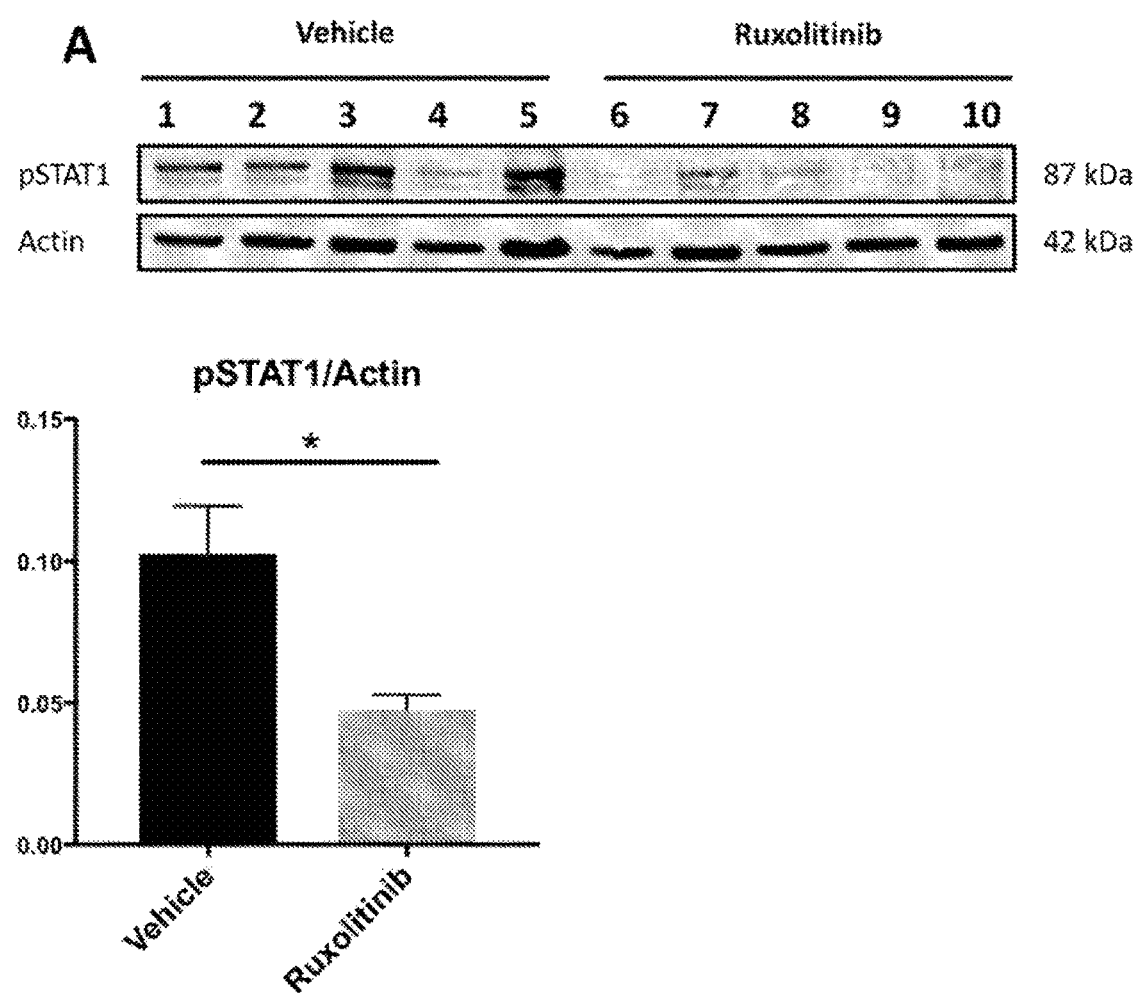
Figure 2:
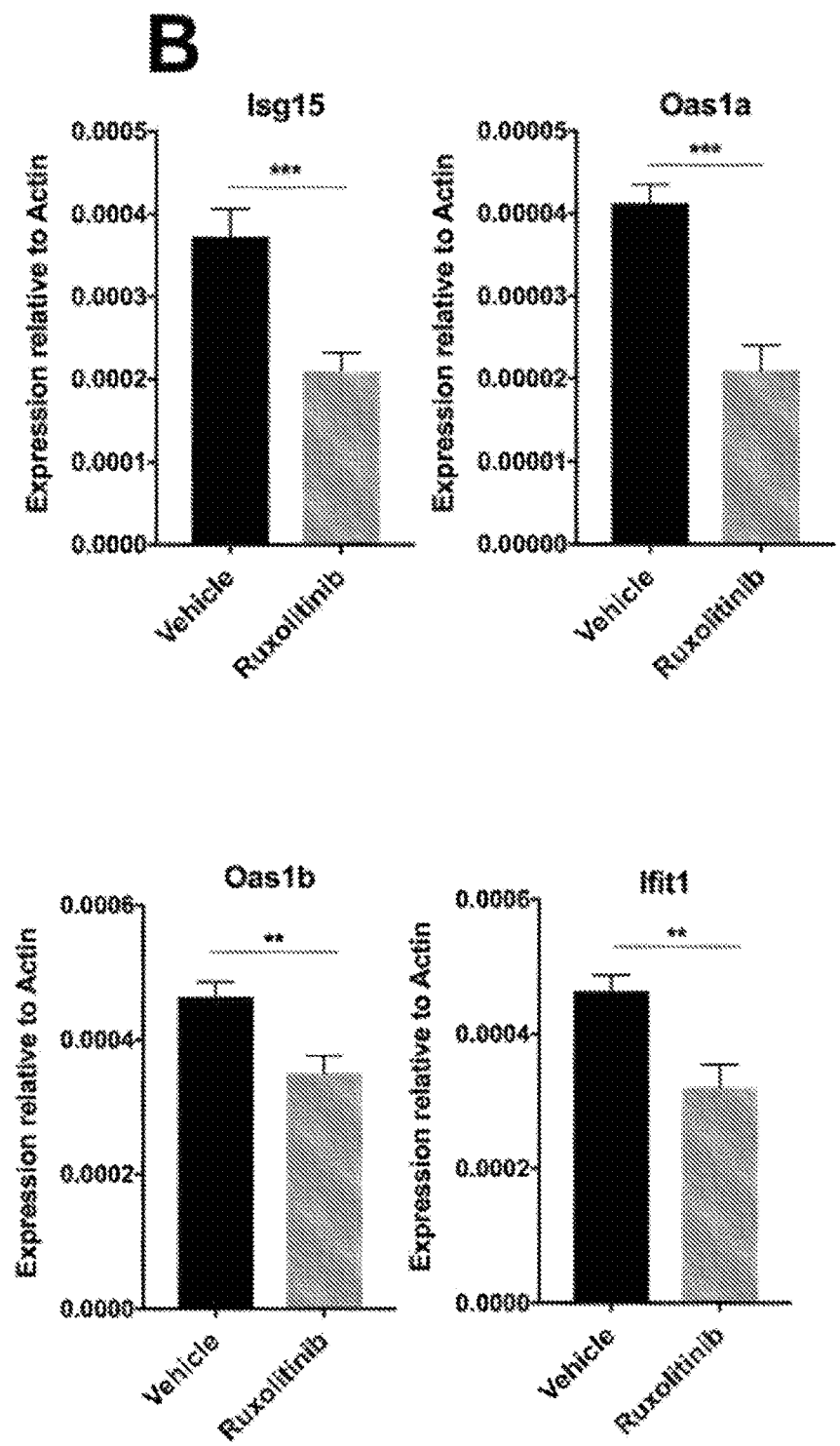
Figure 2:
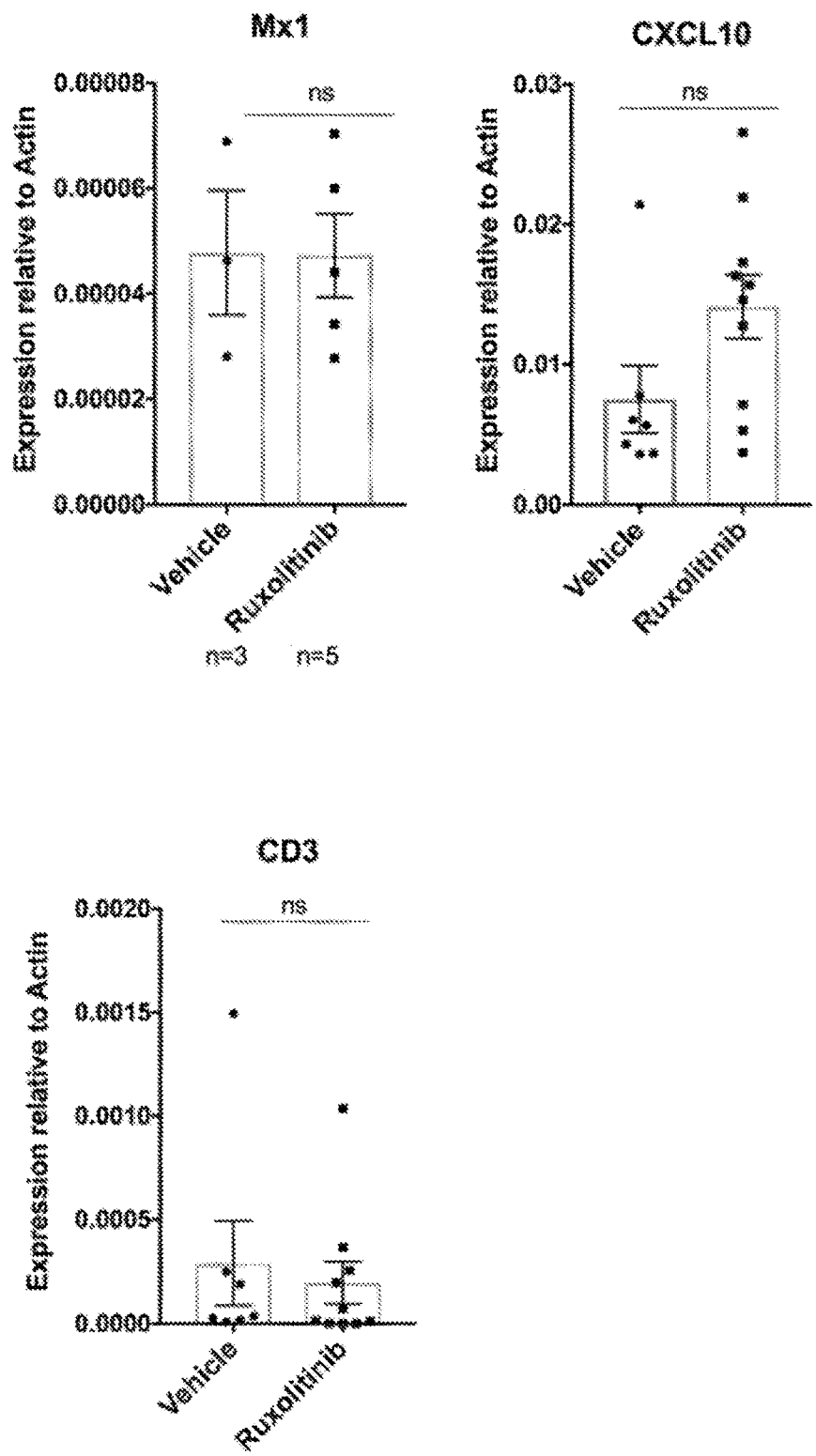

FIG. 2. Ruxolitinib inhibits JAK/STAT signalling and the downstream IFN gene signature in 4 week NOD mice.

(A) NOD mice received 80 mg/kg ruxolitinib (n=5) or vehicle (n=5) daily by oral gavage from 2 to 4 weeks of age. Two hours after last dose of ruxolitinib or vehicle, peripheral blood was stimulated with 100 U/mL IFNγ ex vivo and analysed by Western blot for IFNγ-mediated phosphorylation of STAT1 and housekeeping protein β-actin. The intensity of p-STAT1 as a ratio of β-actin in arbitrary units (mean±SEM) was used to measure p-STAT1. p=0.01 using two-tailed unpaired t test.

(B) NOD mice received 80 mg/kg ruxolitinib (n=10) or vehicle (n=7) daily by oral gavage from 2 to 4 weeks of age; Mx1: n=5 and n=3 respectively. Pancreatic islets were isolated two hours after last dose. IFN-induced genes, chemokine CXCL10 and T cell marker CD3 expression in islets was measured. Expression calculated relative to housekeeping gene β-actin (mean±SEM). Each symbol in scatter plots represents data from an individual mouse. p=0.0008 (Isg15), 0.0002 (Oas1a), 0.0059 (Oas1b) and 0.0063 (Ifit1), using two-tailed unpaired t test. ns=not significant.

Figure 3:
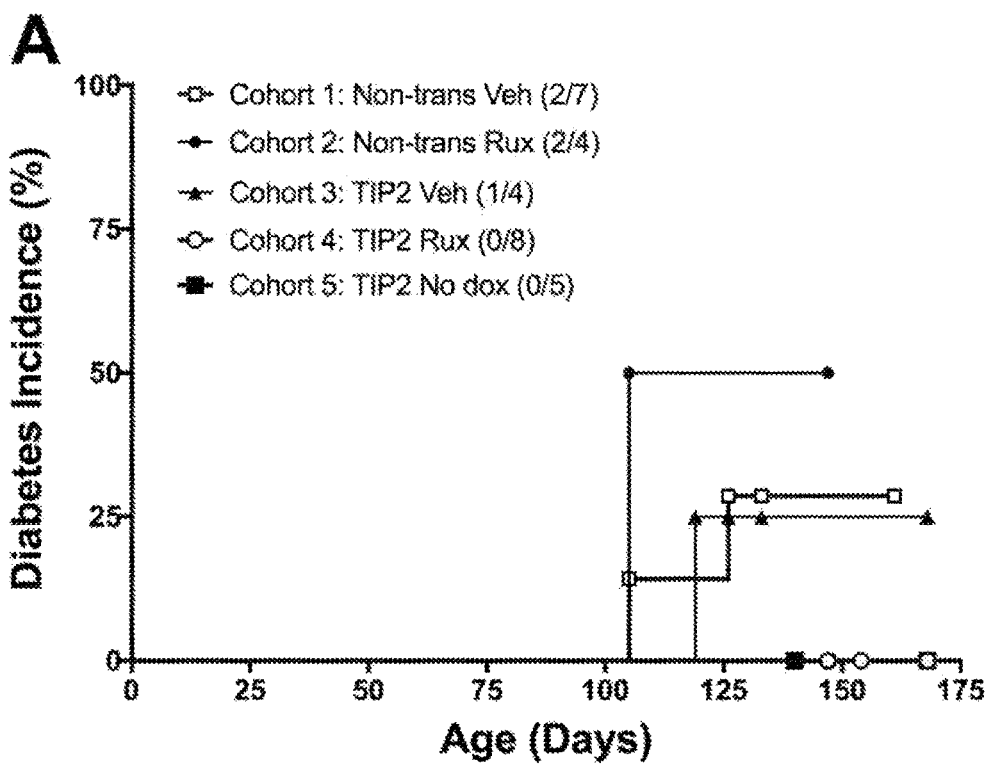
Figure 3:
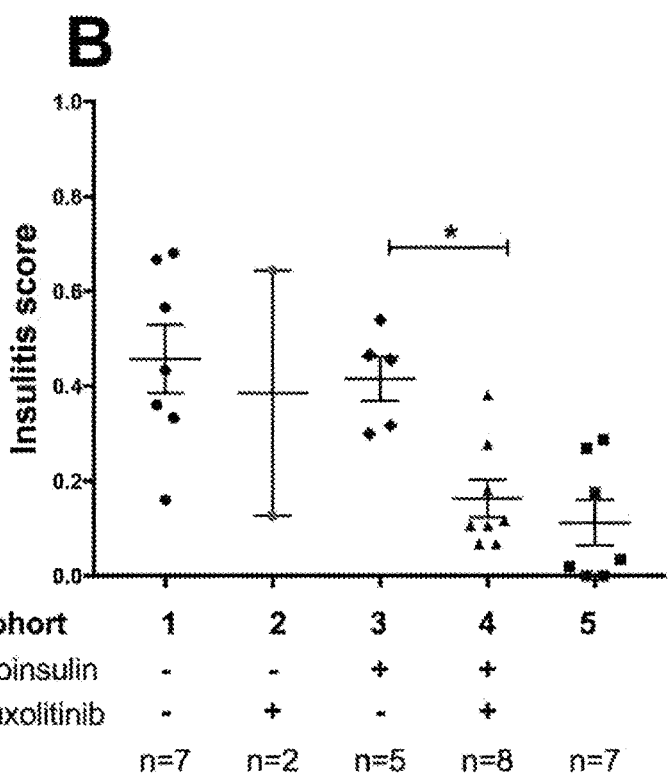
Figure 3:
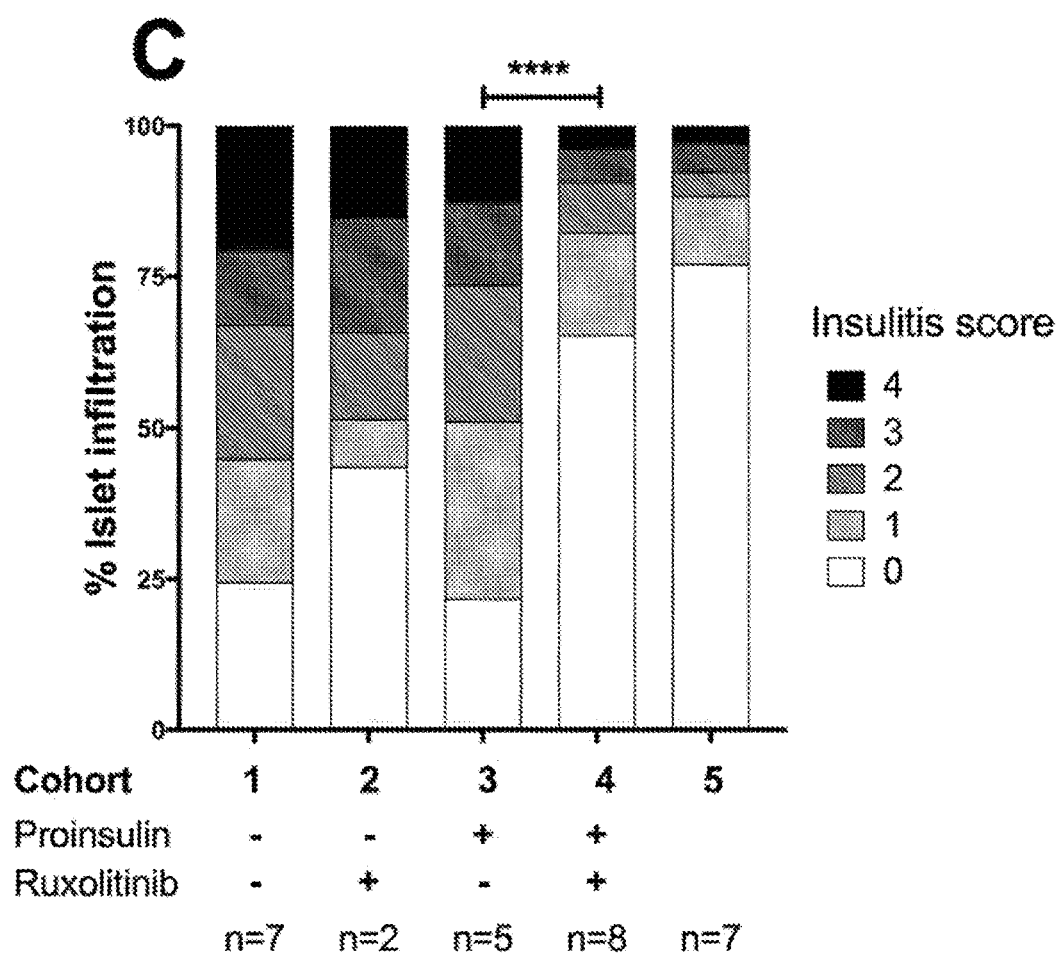

FIG. 3. Diabetes development and insulitis in NOD and TIP2 mice treated with combination therapy.

(A) Incidence of diabetes in cohorts 1 to 5. Mice were monitored for 24 weeks (168 days). Diabetes was diagnosed by positive urine test and confirmed by two consecutive blood glucose measurements. No significant difference in diabetes onset or incidence among the groups by log-rank (Mantel-Cox) analysis.

(B) Individual insulitis scores (mean±SEM) in pancreas sections of NOD and TIP2 mice from all treatment cohorts at 19-28 weeks of age. Each symbol represents data from an individual mouse. p=0.017 cohort 3 vs cohort 4, using one-way ANOVA with Tukey's multiple comparisons test.

(C) Average insulitis in pancreas sections of NOD and TIP2 mice at 19-28 weeks of age. Score 0: p<0.0001 cohort 3 vs cohort 4, using two-way ANOVA with Tukey's multiple comparisons test.

Figure 4:
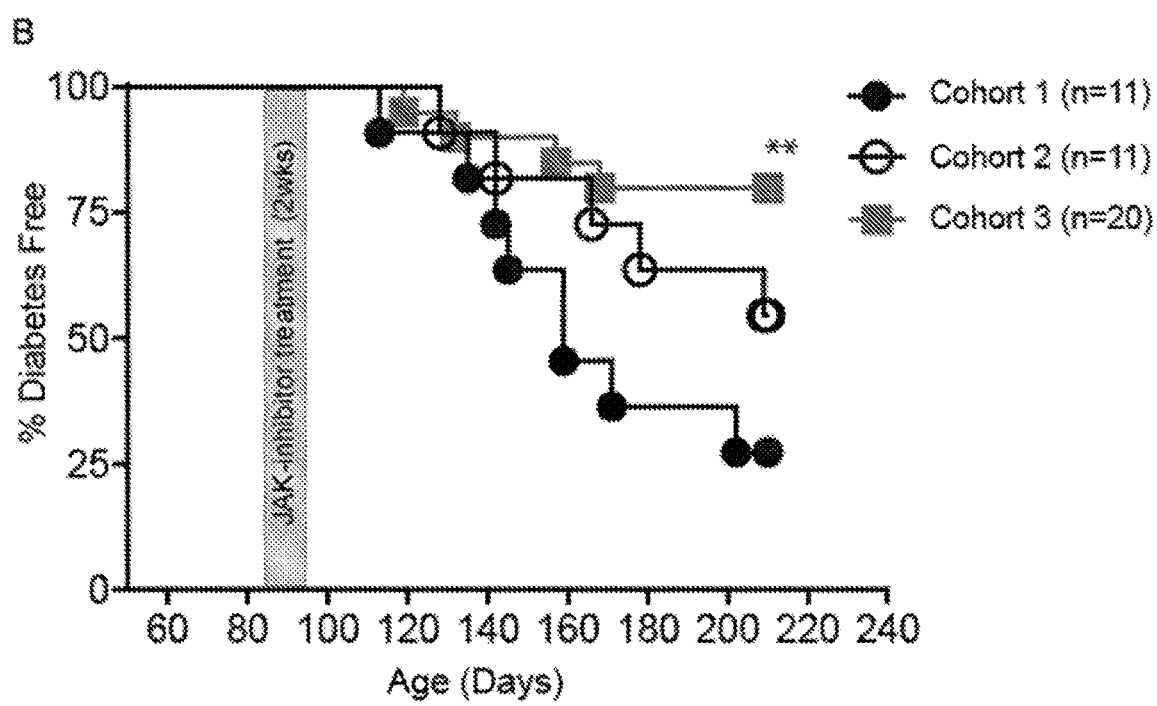

FIG. 4. Diabetes development in TIP2 mice treated with combination therapy.

(A) Study cohorts depicting time of administration and treatment received.

(B) Mice in cohorts 1-3 were treated with JAK inhibitor or vehicle for 2 weeks (shaded bar) and followed for incidence of diabetes. Mice were monitored for 30 weeks (210 days). Diabetes was diagnosed by positive urine test and confirmed by two consecutive blood glucose measurements. **p<0.005. Diabetes incidence curves compared using Log-Rank (Mantel-Cox) test.

Figure 5:
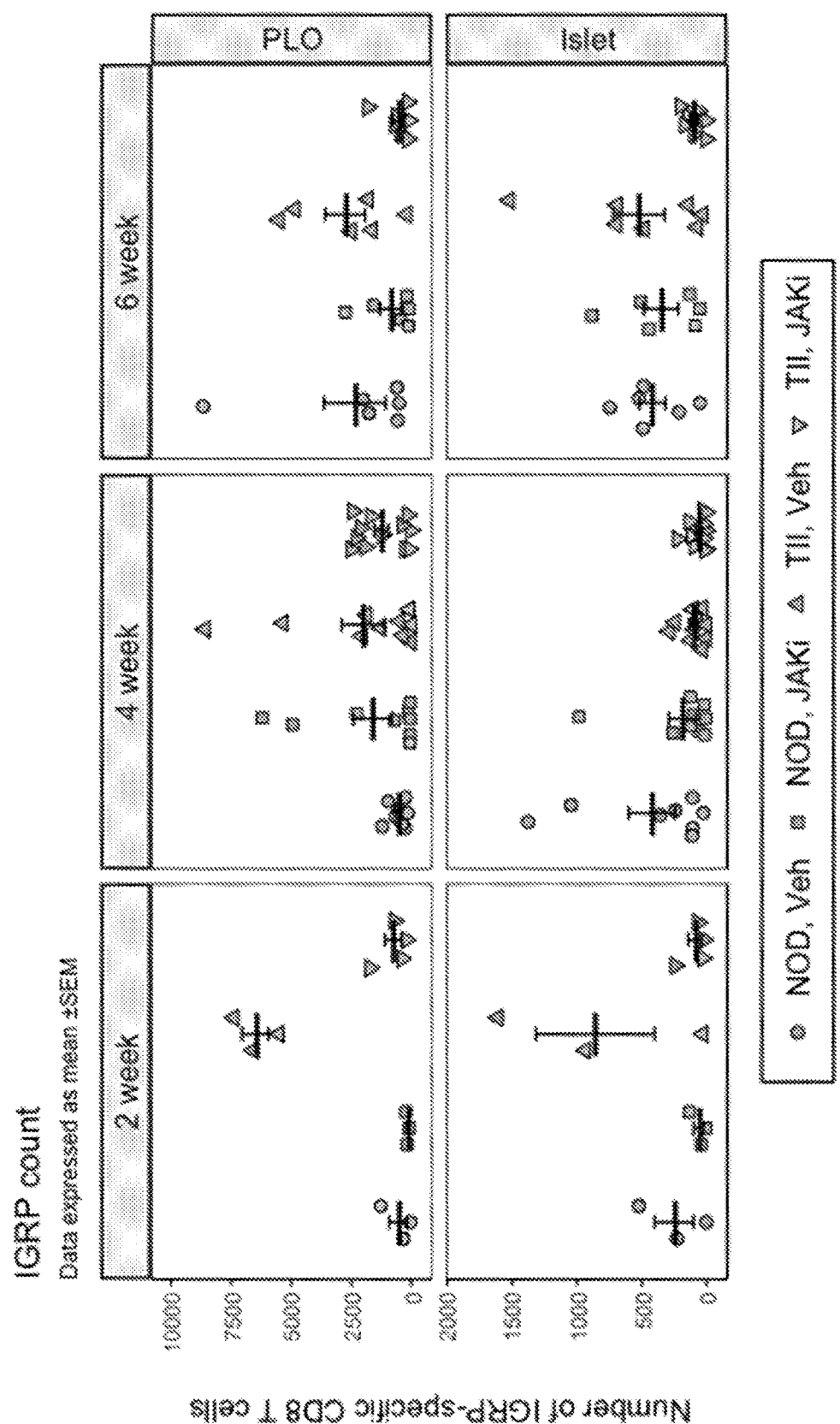

FIG. 5. The proportion of IGRP-specific CD8+ T cells in peripheral lymphoid organs after combination therapy.

IGRP was expressed in TII mice at 10-weeks of age. NOD mice were used as controls without antigen expression. At 13-weeks of age, mice were treated for 2 weeks with vehicle (Veh) or JAK inhibitor (JAKi). Mice were harvested for analysis immediately after treatment (2 week), or after a further 2 or 4 weeks with antigen alone (4 week and 6 week).

The number of IGRP-specific CD8+ T cells in the peripheral lymphoid organs (PLO, top panel) or islets (bottom panel) is shown for each time point.

Statistical significance (one-way ANOVA with Sidak's multiple comparisons test) p=0.02 TII-Veh v TII-JAKi in islets at 6 weeks; p=0.054 TII-Veh v TII-JAKi in PLO at 6 weeks. No significant difference in NOD groups.

DETAILED DESCRIPTION OF THE EMBODIMENTS

It will be understood that the invention disclosed and defined in this specification extends to all alternative combinations of two or more of the individual features mentioned or evident from the text or drawings. All of these different combinations constitute various alternative aspects of the invention.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described. It will be understood that the invention disclosed and defined in this specification extends to all alternative combinations of two or more of the individual features mentioned or evident from the text or drawings. All of these different combinations constitute various alternative aspects of the invention.

All of the patents and publications referred to herein are incorporated by reference in their entirety.

For purposes of interpreting this specification, terms used in the singular will also include the plural and vice versa.

The present inventors have identified methods for preventing or delaying the onset of T1D in at risk individuals, as well as methods for inhibiting, preventing or delaying disease progression in individuals showing early signs of the disease. More specifically, the inventors have shown that it is possible to protect against T1D, or to delay the onset of T1D in individuals who have not yet developed autoimmunity to a pancreatic autoantigen. The present invention therefore has application in preventing T1D in individuals identified through genetic screening to be in high risk categories for the development of T1D (including screening performed based on known family history of T1D).

Further still, the inventors have shown that it is possible to delay or prevent the progression of T1D in individuals who are already displaying signs of disease such as autoantibodies and insulitis. Surprisingly, the inventors have found that the methods of the present invention provide for a long-term deletion of autoreactive T cells after only a brief period of treatment, and even after treatment has ceased, providing significant long-term protection from diabetes development. Moreover, the findings of the inventors indicate that it is possible to significantly delay or prevent the progression of early stage T1D (including with autoimmunity) such that alterations in blood glucose levels and reduction in insulin sensitivity are delayed or prevented.

Delaying the onset of type 1 diabetes prolongs endogenous insulin production and increases the time of exogenous insulin independence. Further, delaying onset of type 1 diabetes is associated with improved long term outcomes for individuals who may eventually succumb to the condition. The present invention therefore provides a significant advantage over the methods of the prior art, which are typically limited to the provision of insulin in individuals who have already progressed to symptomatic T1D.

Without being bound by any theory or mode of action, the inventors believe that the administration of an anti-inflammatory compound, e.g. a JAK inhibitor, inhibits or reverses islet infiltration thereby preventing further generation of memory T cells while reducing inflammation. This reduction inflammation and generation of memory T cells then allows greater induction of tolerance to autoantigen (for example, to proinsulin, IGRP or other autoantigen) during subsequent autoantigen immunotherapy.

Accordingly, the present invention contemplates methods for treating, preventing, delaying the onset of, or delaying progression of, T1D in an individual in need. Typically an individual in need will be an individual who is considered to be at risk for the development of T1D, or is displaying preliminary signs or symptoms of T1D, wherein intervention is desired so as to prevent or delay the onset or further progression of the disease.

As used herein, 'preventing' or 'prevention' with respect to the onset of T1D, is intended to refer to at least the reduction of likelihood of the risk of (or susceptibility to) developing T1D (i.e., causing at least one of the clinical symptoms of the disease not to develop in a patient that may be predisposed to T1D but does not yet experience or display symptoms of T1D).

As used herein, 'preventing' or 'delaying' the progression of T1D is intended to refer to at least slowing down, inhibiting, or reversing the early signs or symptoms of T1D in an individual. For example, preventing or delaying the progression of T1D may include preventing or delaying the onset of autoimmunity in an individual who is at risk of T1D. Alternatively, preventing or delaying the progression of T1D may include reducing the level of autoimmunity to a pancreatic autoantigen in an individual who is at a more advanced state of 'pre-diabetes' (for example, deleting or reducing the number of autoreactive T cells including CD8+ T cells directed to a pancreatic autoantigen). Accordingly, preventing or delaying the progression of T1D may also including prolonging the period of time in which an individual is able to make sufficient levels of endogenous insulin.

The terms 'treatment' or 'treating' of an individual includes the application or administration of a composition, or combination therapy, as described herein, to an individual. with the purpose of delaying, slowing, stabilizing, curing, healing, alleviating, relieving, altering, remedying, less worsening, ameliorating, improving, or affecting the disease or condition, the symptom of T1D. The term "treating" refers to any indication of success in the treatment or amelioration of T1D including any objective or subjective parameter such as abatement; remission; lessening of the rate of worsening; lessening severity of the disease; stabilization, diminishing of symptoms or making the injury, pathology or condition more tolerable to the subject; slowing in the rate of degeneration or decline; making the final point of degeneration less debilitating; or improving a subject's physical or mental well-being.

The development of T1D and progression of the disease is a multi-stage process. In 2015, the JDRF (Juvenile Diabetes Research Foundation), the Endocrine Society and the American Diabetes association, released a scientific statement, establishing the adoption of a staging classification for the development of T1D (Insel et al., 2015, *Diabetes Care*, 38:1964-1974, the entire contents of which are herein incorporated in their entirety). Briefly, the stages are:

Pre-stage 1: genetic susceptibility and genetic risk of T1D

Stage 1: autoimmunity/normoglycaemia/presymptomatic;

Stage 2: autoimmunity+/dysglycaemia/presymptomatic; and

Stage 3: autoimmunity+/dysglycaemia/symptomatic T1D.

The HLA region on chromosome 6 accounts for about 30-50% of the genetic risk of T1D, with the greatest association with HLA class II haplotypes DRB1*0301-DQB1*0201 (DR3-DQ2) and DRB1*0401-DQB1*0302 (DR4-DQ8). The genotype associated with the highest risk for T1D is the heterozygous DR3/4 genotype. HLA class II DRB1*1501 and DQA1*0102-DQB1*0602 confer disease resistance, at least in children younger than 12 years of age.

The remaining genetic risk for T1D can be attributed to the approximately 50 non-HLA genes or loci identified via candidate gene and genome-wide association study approaches, each with modest to small effects on disease risk. The highest non-HLA genetic contribution arises from the INS, PTPN22, CTLA4, and IL2RA genes, with the latter three genes also contributing to susceptibility to other autoimmune diseases. Non-HLA genetic contribution may be acting through immune regulation, although the recent demonstration of gene expression commonly in pancreatic islets and the alternative splicing of several of these gene products in cytokine-stimulated islets have raised the question of whether some of these genes may in part be acting in the β-cell.

Stage 1 represents individuals who have developed two or more T1D-associated islet autoantibodies but are normoglycemic. For children who were screened for genetic risk at birth and reach this stage, the 5-year and 10-year risks of symptomatic disease are approximately 44% and 70%, respectively, and the lifetime risk approaches 100%. The risk at this stage is quite similar in genetically at-risk children and in relatives of individuals with type 1 diabetes. Stage 1 is defined as the presence of two or more islet autoantibodies to insulin, GAD65, IA-2, and/or ZnT8. The mechanisms leading to β-cell autoimmune reactivity have not been completely elucidated. (Pro)insulin, GAD65, IA-2, and ZnT8 and their peptides have been identified as target antigens in T1D. Islet autoantibodies can be measured with standardized, sensitive, and high-throughput assays.

The number of detectable islet autoantibodies correlates with risk. The rate of progression to symptomatic disease in the presence of two or more islet autoantibodies is associated not only with the number of autoantibodies detected and the age of autoantibody seroconversion but also with the magnitude of the autoimmunity titer, affinity of the autoantibody, and the type of autoantibody. Higher titers of insulin and IA-2 autoantibodies are associated with earlier onset of symptomatic type 1 diabetes. The presence of IA-2 or ZnT8 autoantibodies is associated with faster progression to symptomatic disease compared with when both are absent. In first-degree relatives of individuals with type 1 diabetes, IA-2 and/or ZnT8 autoantibody seroconversion is associated with a 5-year progression rate to diabetes of 45%, and the presence of either of these autoantibodies is detected in 78% of progressors to symptomatic disease. Thus, the presence of two or more autoantibodies is used as the major criterion for stage 1. The majority of individuals (85%) with a single autoantibody do not progress to overt symptomatic type 1 diabetes within 10 years. However, some single autoantibody subjects can progress, and progression appears to occur more frequently in children aged <5 years, if the single autoantibody is directed to IA-2 or if the single autoantibody displays higher affinity.

Stage 2 is defined as the presence of β-cell autoimmunity with dysglycemia and is presymptomatic. Stage 2, like stage 1, includes individuals with islet autoantibodies but whose disease has now progressed to the development of glucose intolerance, or dysglycemia, that arises from loss of functional β-cell mass. Dysglycemia in this stage of T1D has been defined in several studies by impaired fasting plasma glucose of ≥100 mg/dL (≥5.6 mmol/L) or ≥110 mg/dL (≥6.2 mmol/L), impaired glucose tolerance with 2-h plasma glucose with a 75-g oral glucose tolerance test (OGTT) of ≥140 mg/dL (≥7.8 mmol/L), high glucose levels at intermediate time points on OGTT (30, 60, 90 min levels of ≥200 mg/dL [≥11.1 mmol/L]), and/or $HbA_{1c}$≥5.7% (≥39 mmol/mol).

Stage 3 represents manifestations of the typical clinical symptoms and signs of diabetes, which may include polyuria, polydipsia, weight loss, fatigue, diabetic ketoacidosis (DKA), and others.

In any embodiment of the invention, the individual may have residual endogenous insulin production although may be classified as falling within Stage 3 (i.e., having clinical symptoms of T1D in addition to dysglycaemia and autoimmunity). The present invention also contemplates methods for treating T1D in such individuals, including for example, to reduce or reverse symptoms of active disease, or enable the individual to be considered "in remission" with respect to symptomatic T1D.

Thus, in any embodiment of the present invention, an individual who is considered at risk of T1D, shows early signs of T1D or who will benefit from the treatments and therapies described herein includes an individual who is classified according to any of the stages 1-3 outlined above, or in "pre-stage 1".

It will be well within the purview of the skilled person to be able to perform the relevant clinical tests to determine whether an individual is at risk of the development of T1D (e.g. using the classification system described herein), and is therefore an individual for whom delay or prevention of T1D may be achieved using the methods and compositions of the present invention.

For example, the skilled person will be familiar with methods for screening for the presence of autoantibodies in an individual, including autoantibodies to one or more β-cell specific antigens. Autoantibodies which may be screened for in accordance with the methods of the present invention, are those which are raised against antigens selected from the group consisting of: Carboxypeptidase H, Chromogranin A, Glutamate decarboxylase (GAD65), Imogen-38, Proinsulin/Insulin, Insulinoma antigen-2 and 26, Islet-specific glucose-6-phosphatase catalytic subunit related protein (IGRP) zinc transporter 8 (ZnT8), and Proinsulin. Preferably, to determine whether an individual is at risk of T1D, the presence of antibodies raised to Islet Cells, Glutamic Acid Decarboxylase, Insulin Autoantibodies (including proinsulin autoantibodies), and IA-2A will be determined.

As used herein, carboxypeptidase H (CPH) also known as carboxypeptidase E (CPE), and enkephalin convertase, is an enzyme that in humans is encoded by the CPE gene. This enzyme catalyzes the release of C-terminal arginine or lysine residues from polypeptides.

Chromogranin A, or parathyroid secretory protein 1 (gene name CHGA) is a member of the granin family of neuroendocrine secretory proteins, i.e., it is located in secretory vesicles of neurons and endocrine cells such as islet beta cell secretory granules in pancreas. In humans, chromogranin A protein is encoded by the CHGA gene. It is present in islet beta cell secretory granules.

As used herein, glutamate decarboxylase is an enzyme that catalyzes the decarboxylation of glutamate to GABA and $CO_2$. In mammals, GAD exists in two isoforms encoded by two different genes—GAD1 and GAD2. These isoforms are GAD67 and GAD65 with molecular weights of 67 and 65 kDa, respectively. Both GAD67 and GAD65 are targets of autoantibodies in people who later develop type 1 diabetes mellitus or latent autoimmune diabetes As used herein, Imogen-38 refers to a 38 kDa islet mitochondrial antigen recognised by T cells from a T1D patient (described in Arden et al., (1996) *J. Clin. Invest.,* 97:551-561).

Islet antigen-2 (IA-2), previously known also as ICA-512, is a major target of islet cell autoantibodies. The protein is found in neural tissue and cells of the pancreatic islets, and its gene has been localized to chromosome 2q35. Autoantibodies to IA-2 are present in up to 80% of children and adolescents at diagnosis of type 1 diabetes. IA-2A generally develops later in the process leading to type 1 diabetes and is therefore associated with more rapid progression. These antibodies are less common in patients who are diagnosed with type 1 diabetes over the age of 30 years. IA-2 may also be referred to as Insulinoma antigen-2 and 2β or tyrosine phosphatase-related islet antigen 2 (IA-2). Seropositivity for IA-2 autoantibody (>0.02 nmol/L) is supportive of a diagnosis of type 1 diabetes, a high risk for future development of diabetes, a current or future need for insulin therapy in patients with diabetes. Negative results do not exclude the diagnosis of or future risk for type 1 diabetes mellitus. The risk of developing type 1 diabetes may be stratified further by testing for: 1) antibodies targeting insulin, glutamic acid decarboxylase, and zinc transporter 8 (ZnT8) and 2) HLA genetic markers.

Islet-specific glucose-6-phosphatase catalytic subunit related protein (IGRP or G6PC2 or glucose-6-phosphatase catalytic subunit 2) is a protein that is selectively expressed in islet beta and alpha cells. IGRP is proposed to act as a negative component of the β-cell glucose sensor, opposing the action of glucokinase and thereby modulating glucose-stimulated insulin secretion. Accordingly, IGRP deficient mice exhibit a 15% reduction of fasting blood glucose but are otherwise metabolically and developmentally indistinguishable from wild-type littermates. Likewise, genome-wide association studies have linked polymorphic variants in G6PC2 to variations in fasting blood glucose levels in humans. IGRP is a major autoantigen in both mouse and human Type I diabetes. Islet inflammation drives the local expansion and development of IGRP specific memory T cells in mice. IGRP-specific T cells circulate at high frequencies in autoimmune diabetes prone NOD mice and in human type 1 diabetic subjects. In mice, circulating IGRP specific T cells report islets pathology. Recent studies have shown that peptides derived from a strain of gut bacteria can stimulate IGRP-reactive T cells.

Zinc transporter 8 (ZnT8), is a member of a large conserved family of cation efflux proteins that plays a vital role in exporting $Zn_{++}$ into the lumen of the beta cell secretory granule where it enables insulin crystallization. ZnT8 autoantibodies are detected in ~70% of newly diagnosed T1D patients. In prediabetic individuals, ZnT8 autoantibodies appear in the prodromal phase years prior to clinical disease and their measurement improves the accuracy of disease risk prediction. Autoreactivity to ZnT8 is unique with regard to a key amino acid residue at position 325 encoded by polymorphisms in the SLC30A8 gene, either arginine (R), tryptophan (W) or glutamine (Q). Prediabetic children harboring ZnT8 autoantibodies that are homozygous for either the R or W variant allele carry the greatest disease risk. Sensitive and specific ZnT8 autoantibody assays have been developed to capture antibodies targeting the ZnT8 major epitopes.

Proinsulin is the prohormone precursor to insulin made in the beta cells of the islets of Langerhans, specialized regions of the pancreas. In humans, proinsulin is encoded by the INS gene. Proinsulin is the final single chain protein structure secreted by cells before cleavage into mature insulin. In accordance with the methods of the present invention, autoantibodies to both proinsulin and insulin may be used in determining whether an individual has developed autoimmunity indicative of T1D risk.

In order to determine the presence and level of the autoantibodies herein described in an individual (for example, to determine risk of T1D), assays may be performed on plasma or serum samples from individuals using standard techniques and commercially available reagents. For example, in any embodiment of the present invention, the antibodies may be measured using standard radiobinding assays (for example, from DLD Diagnostika, Germany) or electrochemiluminescence (ECL) assays (for example, as described in Steck et al., (2016), *Diabetes Technol Ther,* 18:410-414, the entire contents of which are herein incorporated in their entirety). Alternatively, standard immunoassay methods including enzyme-linked immunosorbent assay (ELISA) may also be used. Commercially produced ELISA kits and reagents for determining autoantibody levels in patient samples can be obtained, for example, from RSR Ltd, (Cardiff, UK) or Launch Diagnostics (Longfield, UK).

The skilled person will also be familiar with the threshold levels of seropositivity for each autoantibody indicative of risk of T1D and conventions for the measurement of islet autoantibodies (for example, as described in The Diabetes Antibody Standardisation Program, DASP, see Torn et al., (2008) *Diabetalogia,* 51: 846-52 and Schlosser et al., (2011) *Diabetes Care,* 34: 2410-2412).

The skilled person will further be familiar with methods for genetic screening to identify whether the individual has a "high risk HLA genotype" including, for example, any of the HLA genotypes described herein and which are associated with risk of T1D. For example methods for screening for at risk HLA genotypes, including those defined herein, will be well within the purview of the skilled person.

The skilled person will also be familiar with methods for determining whether an individual is "normoglycaemic" or has symptoms of "dysglycaemia", which may assist in determining the stage of T1D development, and whether the individual is displaying symptoms of T1D. Methods for determining blood glucose levels, including after oral glucose challenge, will be familiar to the skilled person.

As used herein, "normoglycaemia" (or euglycaemia) refers to a normal blood glucose level (i.e., one which is not dysglycaemic or hyperglycaemic as herein defined).

As used herein, dysglycemia refers to impaired fasting plasma glucose of ≥100 mg/dL (≥5.6 mmol/L) or ≥110 mg/dL (≥6.2 mmol/L), impaired glucose tolerance with 2-h plasma glucose with a 75-g oral glucose tolerance test (OGTT) of ≥140 mg/dL (≥7.8 mmol/L), high glucose levels at intermediate time points on OGTT (30, 60, 90 min levels of ≥200 mg/dL [≥11.1 mmol/L]), and/or $HbA_{1c}$ 5.7% (≥39 mmol/mol).

The term "hyperglycaemia" as used herein refers generally to blood glucose levels that are above normal. Hyperglycaemia can be determined by any measure accepted and utilized by those of skill in the art. Currently, in humans, normal blood glucose is considered to be between about 70 and 120 mg/dl (3.9-6.6 mmol/L), but varies depending on the fasting state. Before a meal, blood glucose can range from about 80 to 120 mg/dl (4.4-6.6 mmol/L), whereas two hours after a meal, blood glucose can be at or below about 180 mg/dl (10 mmol/L). Additionally, in fasted individuals, normal blood glucose is below about 110 mg/dl (6.1 mmol/L). A subject having a blood glucose value of about 126 mg/dl (7 mmol/L) or greater is generally considered hyperglycaemic, and a subject whose blood glucose is above about 200 mg/dl (11.1 mmol/L) is generally considered diabetic.

The skilled person will also be able to determine whether an individual is "presymptomatic" or has commenced exhibiting symptoms of clinical manifestations of T1D. For example, symptoms of polyuria, polydipsia, weight loss, fatigue and diabetic ketoacidosis are symptoms of T1D. As used herein, polyuria refers to excessive or abnormally large production or passage of urine (greater than 2.5 or 3 L over 24 hours in adults). Frequent urination is sometimes included by definition but is nonetheless usually an accompanying symptom.

As used herein, polydipsia refers to excessive thirst, and may also be accompanied by dry mouth.

Diabetic ketoacidosis (DKA) is related to hyperglycaemia, is associated with illness or very high blood glucose levels in type 1 diabetes and can be a sign of insufficient insulin production. In the absence of sufficient insulin, the body burns fat for energy instead, which may lead to accumulation of ketones in the blood (and which also may appear in the urine). DKA generally refers to high blood glucose levels and moderate to heavy ketones in the urine. Other symptoms or indicators of DKA include rapid breathing, flushed cheeks, abdominal pain, sweet acetone (similar to paint thinner or nail polish remover) smell on the breath, vomiting and dehydration.

The skilled person will also be familiar with other methods for determining whether an individual is at risk of or is displaying early signs of T1D such as by measuring the frequency of CD4+ or CD8+ T-cells which are specific for a pancreatic antigen. This may include detecting the frequency of autoreactive T cells, including CD8+ T cells to one or more of proinsulin, islet-specific glucose-6-phosphatase catalytic subunit related protein (IGRP), glutamate decarboxylase (GAD), islet-antigen 2 (IA-2) and zinc transporter 8 (ZnT8).

The present invention relates to methods which include providing in an individual a combination of an anti-inflammatory compound, and a pancreatic autoantigen (such as proinsulin), or a variant or derivative thereof.

As will be generally understood by the skilled person, an anti-inflammatory compound is a compound that reduces inflammatory signal cascades. This may include, for example, reducing circulating cytokines or blocking the signalling cascade elicited by those cytokines, including interferons (IFNs). Interferons are produced in response to pathogens, including viruses, bacteria and foreign nucleic acids. In children genetically predisposed to T1D, a type I IFN-induced gene signature has been observed to arise before the appearance of anti-islet autoantibodies. (In other words, increased expression of genes that are regulated by Type I IFN has been observed). Without wishing to be bound by theory, the present inventors believe that reducing the IFN-induced inflammatory response in at-risk children, may increase the likelihood of successful auto-antigen immunotherapy.

Preferably, the anti-inflammatory compound is one which inhibits or reverses islet infiltration thereby preventing further generation of memory T cells while reducing inflammation. Without being bound by theory, it is thought that this reduction inflammation and generation of memory T cells then allows greater induction of tolerance to proinsulin.

In any embodiment of the present invention, the anti-inflammatory compound is an inhibitor of proinflammatory cytokine-regulated gene expression (i.e., any molecule which inhibits signalling of inflammatory cytokines, thereby reducing inflammatory signalling cascades).

In any embodiment of the present invention, the inhibitor of pro-inflammatory cytokine-regulated gene expression is a Janus kinase inhibitor, also known as a JAK inhibitor. JAK inhibitors are compounds that inhibit the activity of one or more of the Janus kinase family of enzymes (JAK1, JAK2, JAK3, TYK2), thereby interfering with the JAK-STAT signaling pathway.

Janus kinase (JAK) is a family of intracellular non-receptor tyrosine kinases, ranging from 120-140 kDa, that transduce cytokine-mediated signals via the JAK-STAT pathway. The JAK family plays a role in the cytokine-dependent regulation of proliferation and function of cells involved in immune response. Currently, there are four known mammalian JAK family members: JAK1, JAK2, JAK3 and TYK2.

JAK1, JAK2 and TYK2 are ubiquitously expressed whereas JAK3 is expressed in the myeloid and lymphoid lineages. The JAK family members are non-receptor tyrosine kinases that associate with many hematopoietin cytokines, receptor tyrosine kinases and GPCR's.

JAK2 is a cytoplasmic protein-tyrosine kinase that catalyzes the transfer of the gamma-phosphate group of adenosine triphosphate to the hydroxyl groups of specific tyrosine residues in signal transduction molecules. JAK2 mediates signaling downstream of cytokine receptors after ligand-induced autophosphorylation of both receptor and enzyme. The main downstream effectors of JAK2 are a family of transcription factors known as signal transducers and activators of transcription (STAT) proteins.

As used herein, a 'JAK inhibitor' is any compound that inhibits the expression or activity of a janus kinase. For example, the inhibitor of JAK may inhibit JAK mediated signalling. Typically, the inhibitor of JAK directly inhibits the enzymatic (kinase) activity of JAK. The JAK inhibitor may inhibit a JAK by up to 10%, 20%, 30%, 40%, 50%, 60%, 70%, 80%, 90% or 100% (of values intermediate to those recited).

Preferably, the inhibitor binds to the active site of JAK. More preferably, the inhibitor of JAK competes with, or prevents the binding of a substrate of JAK for binding to JAK. Given that cytokine signalling depends on JAK activity, a compound that inhibits the activity of a JAK will also alter or dampen cytokine signalling.

Examples of suitable JAK inhibitors that may be used in accordance with the present invention include: ruxolitinib (trade name Jakafi/Jakavi, also known as INCB018424), tofacitinib (trade name Xeljanz/Jakvinus, also known as CP-690,550), Oclacitinib (trade name Apoquel), Baricitinib (LY3009104, INCB28050), Filgotinib, Gandotinib (LY2784544), Lestaurtinib (CEP-701), Momelotinib (CYT-387), Pacritinib (SB1518), Upadacitinib, Peficitinib, TG101348 (SAR302503), AZD1480, BMS-911543, XL019, and NS018.

Ruxolitinib (Jakafi™, INCB018424) is a potent, orally available, selective inhibitor of both JAK1 and JAK2 of the JAK-STAT signaling pathway. Ruxolitinib was initially developed to target the constitutive activation of the JAK-STAT pathway in patients with myeloproliferative neoplasms (MPNs). Ruxolitinib phosphate has the CAS number: 1092939-17-7.

CYT387 is an inhibitor of Janus kinases JAK1 and JAK2, acting as an ATP competitor with IC50 values of 11 and 18 nM, respectively. The inhibitor is significantly less active towards other kinases, including JAK3 (IC50=0.16 µM).

TG101348 (SAR302503) is an orally available inhibitor of Janus kinase 2 (JAK-2) developed for the treatment of patients with myeloproliferative diseases including myelofibrosis. TG101348 acts as a competitive inhibitor of protein kinase JAK-2 with IC50=6 nM; related kinases FLT3 and RET are also sensitive, with IC50=25 nM and IC50=17 nM, respectively. Significantly less activity was observed against other tyrosine kinases including JAK3 (IC50=169 nM). In treated cells, the inhibitor blocks downstream cellular signaling (JAK-STAT) leading to suppression of proliferation and induction of apoptosis.

AZD1480 is an orally bioavailable inhibitor of Janus-associated kinase 2 (JAK2) with potential antineoplastic activity. JAK2 inhibitor AZD 1480 inhibits JAK2 activation, leading to the inhibition of the JAK/STAT (signal transducer and activator of transcription) signaling including activation of STAT3.

Lestaurtinib (CEP-701) is a tyrosine kinase inhibitor structurally related to staurosporine.

Figure 1:
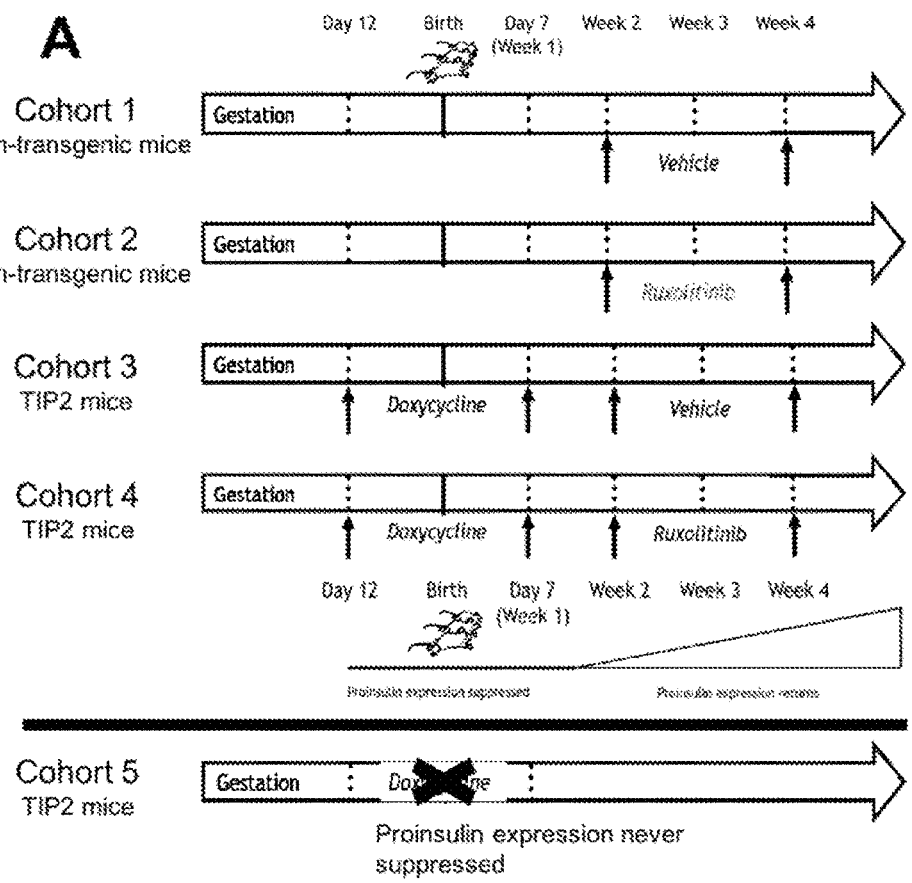
FIG. 1. Doxycycline-dependent temporal and cell-specific proinsulin expression in TIP2 mice.
Figure 1:
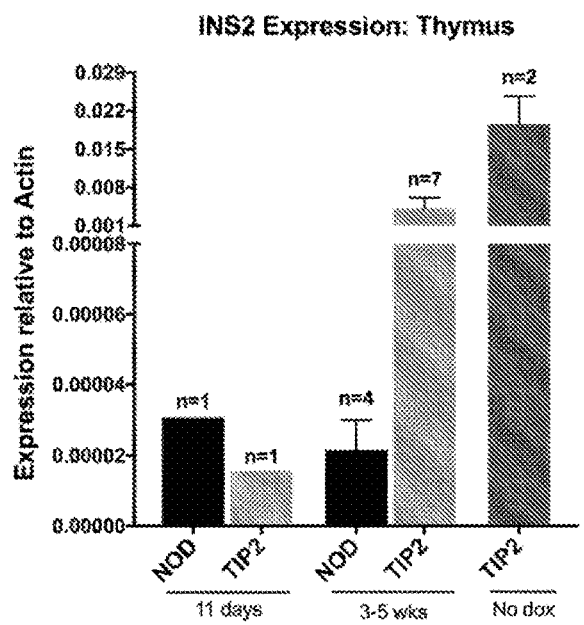

Tofacitinib (Xeljanz®, tascotinib, or CP-690,550) is a known inhibitor of JAK1 and JAK3. Data described herein demonstrate that tofacitinib also binds to the ATP-binding pocket of JAK2 (FIG. 1A). Tofacitinib is used to inhibit JAK-STAT signaling, and is used for treatment of rheumatoid arthritis.

Pacritinib (SB 1815) is an orally bioavailable inhibitor of JAK2 and the JAK2 mutant JAK2V617F with potential antineoplastic activity. Pacritinib competes with JAK2 for ATP binding, which may result in inhibition of JAK2 activation, inhibition of the JAK-STAT signaling pathway, and therefore caspase-dependent apoptosis. Pacritinib is currently investigated for its utility in treatment of myeloproliferative disorders.

Baricitinib (LY3009104, INCB28050) is an orally bioavailable inhibitor of JAK1 and JAK2 with IC50=5.9 nm and IC50=5.7, nm respectively. Baricitinib preferentially inhibits JAK1 and JAK2, with 10-fold selectivity over Tyk2 and 100-fold over JAK3. The drug has shown efficacy in treatment of rheumatoid arthritis.

BMS-911543 a potent and selective small-molecule inhibitor of the Janus kinase (JAK) family member, JAK2 that has shown anti-proliferative activity in patients with JAK2V617F positive myeloproliferative neoplasms.

LY2784544 has been identified as a highly selective small molecule inhibitor of JAK2-V617F, and has been investigated for treatment efficacy in patients with myeloproliferative neoplasms.

XL019 is an orally bioavailable inhibitor of Janus-associated kinase 2 (JAK2) with potential antineoplastic activity. XL019 inhibits the activation of JAK2 as well as the mutated form JAK2V617F, which may result in the inhibition of the JAK-STAT signaling pathway and may induce apoptosis.

NS018 is a potent JAK2 inhibitor with some inhibition of Src-family kinases. NS018 has been shown to be highly active against JAK2 with a 50% inhibition (IC50) of <1 nM, and had 30-50-fold greater selectivity for JAK2 over other JAK-family kinases.

The skilled person will be familiar with methods for determining whether the provision or administration of a JAK inhibitor, or other anti-inflammatory molecule has sufficiently reduced cytokine signalling and the inflammatory state of an individual requiring treatment in accordance with the present invention.

For example, observing reduced phosphorylation of STAT (Signal Transducer and Activator of Transcription) proteins in peripheral blood samples, following stimulating with IFN may be indicative of a reduction in cytokine signalling resulting from the action of JAK inhibitors. The skilled person will be familiar with standard techniques for measuring cytokine signalling in peripheral blood mononucleocytes (including the use of commercially available assays, such as "Phospho-STAT Cellular Assays" from Cisbio, USA and the "Cell-Based phospho-STAT ELISA Sampler Kit" from Sigma-Aldrich, MO, USA).

Other measures for observing reduction in systemic or localised inflammation may be performed (for example, by visual inspection of pancreatic inflammation using MRI or other imaging technique, or measuring expression of IFN-induced genes in pancreatic islets or other biological sample obtained from the individual, using standard RT-PCR techniques).

In addition to the administration of an anti-inflammatory compound, the present invention also includes providing in an individual, a pancreatic autoantigen, such as proinsulin, or a derivative or variant thereof. Without wishing to be bound by theory, the present inventors believe that the exposing an individual, at risk of the development of T1D, to an autoantigen (for example, in the form of proinsulin) during a critical period of development, may impart long-lasting protection from diabetes. In other words, brief exposure to a pancreatic autoantigen, during the development of an at-risk individual's immune repertoire, may assist in providing or restoring tolerance to the autoantigen in the individual, thereby preventing or delaying the onset of T1D in that individual.

As such, the present invention contemplates the provision of autoantigen-specific immunotherapy, in conjunction with anti-inflammatory therapy, to individuals at risk of T1D. In particular, the present invention contemplates provision of proinsulin-specific immunotherapy, in conjunction with anti-inflammatory therapy.

Various autoantigens associated with T1D are previously described herein. The present invention contemplates the provision of a pancreatic autoantigen selected from proinsulin, islet-specific glucose-6-phosphatase catalytic subunit related protein (IGRP), glutamate decarboxylase (GAD), islet-antigen 2 (IA-2) or zinc transporter 8 (ZnT8) to an individual, in conjunction with anti-inflammatory therapy. Preferably, the autoantigen is proinsulin.

As used herein, proinsulin refers to the prohormone precursor to insulin made in the beta cells of the islets of Langerhans, specialized regions of the pancreas. In humans, proinsulin is encoded by the INS gene. The islets of Langerhans only secrete between 1% and 3% of proinsulin intact. However, because proinsulin has a longer half-life than insulin, it can account for anywhere from 5-30% of the insulin-like structures circulating in the blood. Additionally, while proinsulin and insulin have structural differences, proinsulin does demonstrate some affinity for the insulin receptor. Due to the relative similarities in structure, proinsulin can produce between 5% and 10% of the metabolic activity similarly induced by insulin.

Proinsulin is the final single chain protein structure secreted by cells before cleavage into mature insulin.

Examples of proinsulin polypeptides include wild-type human proinsulin and polypeptides having at least about 60%, at least about 70%, at least about 80%, at least about 90%, at least about 95%, at least about 96%, at least about 97%, at least about 98%, or at least about 99% sequence identity with such wild-type human proinsulin.

Exemplary human proinsulin polypeptides are described, e.g., in UniProtKB—P01308 and links therein.

Additional exemplary proinsulin nucleotide sequences are represented by the coding sequences of NCBI accession numbers AY899304, NM_000207 (transcript variant 1); NM_001185097 (transcript variant 2); NM_001 185098 (transcript variant 3), NMJ301291897 (transcript variant 4), and partial functional sequences thereof. Exemplary proinsulin amino acid sequences include those encoded by any one of the above proinsulin nucleic acid sequences.

As used herein variants and derivatives of proinsulin include the proinsulin precursor molecule, preproinsulin (amino acids 1-110 of GenBank Accession No. NP_000198) and the derivative molecule, insulin.

The present invention also contemplates the use of homologs of human proinsulin or insulin, including but not necessarily limited to antigens derived from non-human species such as mouse or rat. The mouse or rat proinsulin or insulin may be (derived from) proinsulin-1 or proinsulin-2 or a combination thereof.

As used herein, IGRP refers to Glucose-6-phosphatase 2 (G-6-Pase 2 or G6PC2), which is a protein of uncertain function. Exemplary amino acid sequences of human IGRP, including of the splice variant forms, are annotated in UniProt KB accession number Q9NQR9 and links therein. Additional information is found in OMIM under accession number 608058. Additional IGRP nucleotide sequences are represented by the coding sequences of Hs.283963, NP_001075155.1, NM_001081686.1 [Q9NQR9-3] NP_066999.1, and NM_021176.2 [Q9NQR9-1].

Glutamate decarboxylase (GAD), exists in two isoforms with molecular weights of 67 and 65 kDa (GAD67 and GAD65), which are encoded by two different genes on different chromosomes (GAD1 and GAD2 genes, respectively). GAD67 and GAD65 are expressed in the brain where GABA is used as a neurotransmitter, and they are also expressed in the insulin-producing β-cells of the pancreas, in varying ratios depending upon the species. Exemplary amino acid sequences of GAD are described in UniProt KB under accession number Q99259 and Q05329. Nucleic acid sequences of GAD1 and GAD2 are provided under NCBI accession numbers: NM_000818.2, NM_001134366.1, NP_000808.2, NM_000817.2 [Q99259-1], NM_013445.3 [Q99259-3], XP_005246501.1, XM_005246444.2 [Q99259-3], XP_011509224.1, XM_011510922.1 [Q99259-1], XP_016859245.1, XM_017003756.1 [Q99259-1], XP_016859247.1, and XM_017003758.1 [Q99259-3].

Islet-antigen 2 (IA-2) is also known as Receptor-type tyrosine-protein phosphatase-like N, or PTPRN). Exemplary amino acid sequences of human IA-2 can be found under UniProt KB accession number Q16849. Exemplary nucleotide sequences are represented by the coding sequences of NM_001199763, NM_001199764 and NM_002846

Zinc transporter 8 (ZnT8) is encoded by the gene SLC30A8 in humans. Exemplary amino acid sequences of ZnT8 and variants thereof can be found under UniProt KB accession number Q8IWU4. Exemplary nucleotide sequences are represented by the coding sequences of NP_001166282.1, NM_001172811.1 [Q8IWU4-2], NP_001166284.1, NM_001172813.1 [Q8IWU4-2], NP_001166285.1, NM_001172814.1 [Q8IWU4-2], NP_001166286.1, NM_001172815.2 [Q8IWU4-2], NP 776250.2, and NM_173851.2 [Q8IWU4-1].

The pancreatic antigen (e.g., proinsulin, islet-specific glucose-6-phosphatase catalytic subunit related protein (IGRP), glutamate decarboxylase (GAD), islet-antigen 2 (IA-2) and zinc transporter 8 (ZnT8) for use in accordance with the methods of the present invention, may be recombinant or synthetic, or isolated or purified from a natural source.

As used herein, the term "recombinant" shall be understood to mean the product of artificial genetic recombination. Accordingly, in the context of a recombinant protein comprising or consisting of proinsulin, this term does not encompass a proinsulin naturally-occurring within a subject's body. However, if such a protein is isolated, it is to be considered an isolated protein comprising or consisting of proinsulin. Similarly, if nucleic acid encoding the protein is isolated and expressed using recombinant means, the resulting protein is a recombinant protein comprising or consisting of proinsulin. A recombinant protein also encompasses a protein expressed by artificial recombinant means when it is within a cell, tissue or subject, e.g., in which it is expressed.

The term "protein" shall be taken to include a single polypeptide chain, i.e., a series of contiguous amino acids linked by peptide bonds or a series of polypeptide chains covalently or non-covalently linked to one another (i.e., a polypeptide complex). For example, the series of polypeptide chains can be covalently linked using a suitable chemical or a disulphide bond. Examples of non-covalent bonds include hydrogen bonds, ionic bonds, Van der Waals forces, and hydrophobic interactions.

The term "polypeptide" or "polypeptide chain" will be understood from the foregoing paragraph to mean a series of contiguous amino acids linked by peptide bonds.

The term "derivatives" includes fragments, parts, portions, chemical equivalents, mutants, homologs and analogs of proinsulin. Analogs may be derived from natural synthetic or recombinant sources and include fusion proteins. Chemical equivalents of proinsulin can act as a functional analog of proinsulin. Chemical equivalents may not necessarily be derived from the pancreatic antigen but may share certain conformational similarities. Alternatively chemical equivalents may be specifically designed to mimic certain physiochemical properties of the pancreatic antigen. Chemical equivalents may be chemically synthesised or may be detected following, for example, natural product screenings. Preferably, the derivatives or variants of the autoantigens describes herein include at least one effector T cell epitope.

Derivatives include one or more insertions, deletions or substitutions of amino acids. Amino acid insertional derivatives include amino and/or carboxylic terminal fusions as well as intrasequence insertions of single or multiple amino acids. Insertional amino acid sequence variants are those in which one or more amino acid residues are introduced into a predetermined site although random insertion is also possible with suitable screening of the resulting product. Deletional variants are characterised by the removal of one or more amino acids from the sequence. Substitutional amino acid variants are those in which at least one residue in the sequence has been removed and a different residue inserted in its place. Additions to amino acid sequences include fusions with other peptides or polypeptides.

The term "isolated" in relation to a protein or polypeptide means that by virtue of its origin or source of derivation is not associated with naturally-associated components that accompany it in its native state; is substantially free of other proteins from the same source. A protein may be rendered substantially free of naturally associated components or substantially purified by isolation, using protein purification techniques known in the art. By "substantially purified" is meant the protein is substantially free of contaminating agents, e.g., at least about 70% or 75% or 80% or 85% or 90% or 95% or 96% or 97% or 98% or 99% free of contaminating agents.

In any embodiment of the present invention, the proinsulin, or derivative or variant thereof is provided in the individual by administration of proinsulin directly to the individual. For example, the proinsulin may be administered intravenously, intranasally, by inhalation, intramuscularly or subcutaneously. Similarly, the present invention contemplates the direct administration of insulin and variants thereof to an individual.

Generally, daily oral doses of antigen will be from about 0.01 mg/kg per day to 1000 mg/kg per day. Small doses (0.01-1 mg) may be administered initially, followed by increasing doses up to about 1000 mg/kg per day. In the event that the response in a subject is insufficient at such doses, even higher doses (or effective higher doses by a different, more localised delivery route) may be employed to the extent patient tolerance permits. A single dose may be administered or multiple doses may be required on an hourly, daily, weekly or monthly basis. Effective amounts of antigen vary depending on the individual but may range from about 0.1 μg to about 20 mg, preferably from about 1 μg to about 10 mg and more preferably from about 1 μg to 5 mg per dose.

A pharmaceutical composition comprising a pancreatic autoantigen, or variant or derivative thereof, may also be formulated as inhaled or intranasal formulations, including sprays, mists, or aerosols. The inhaled formulation may be for application to the upper (including the nasal cavity, pharynx and larynx) and/or lower respiratory tract (including trachea, bronchi and lungs). For inhalation formulations, the composition or combination provided herein may be delivered via any inhalation methods known to a person skilled in the art. Such inhalation or intranasal methods and devices include, but are not limited to, metered dose inhalers with propellants such as HFA or propellants that are physiologically and environmentally acceptable.

A particularly preferred form of administration of proinsulin, or variant or derivative thereof is intranasal administration via an aerosol spray, drip or vapour.

Other suitable devices are breath operated inhalers, multidose dry powder inhalers and aerosol nebulizers. Aerosol formulations for use in the subject method typically include propellants, surfactants and co-solvents and may be filled into conventional aerosol containers that are closed by a suitable metering valve. Different devices and excipients can be used depending on whether the application is to the upper (including the nasal cavity, pharynx and larynx) or lower respiratory tract (including trachea, bronchi and lungs) and can be determined by those skilled in the art. Further, processes for micronisation and nanoparticle formation for the preparation of compounds described herein for use in an inhaler, such as a dry powder inhaler, are also known by those skilled in the art.

Inhalant compositions may comprise liquid or powdered compositions containing the active ingredient(s) that are suitable for nebulization and intrabronchial use, or aerosol compositions administered via an aerosol unit dispensing metered doses. Suitable liquid compositions comprise the active ingredient in an aqueous, pharmaceutically acceptable inhalant solvent such as isotonic saline or bacteriostatic water. The solutions are administered by means of a pump or squeeze-actuated nebulized spray dispenser, or by any other conventional means for causing or enabling the requisite dosage amount of the liquid composition to be inhaled into the patient's nose or lungs. Suitable formulations, wherein the carrier is a liquid, for administration, as for example, a nasal spray or as nasal drops, include aqueous or oily solutions of the active ingredient. Examples of inhalation drug delivery devices are described in Ibrahim et al. Medical Devices: Evidence and Research 2015:8 131-139, are contemplated for use in the present invention.

Proinsulin, or derivatives or variants thereof, may also be formulated for intradermal administration. Examples of suitable formulations and methods for intradermal injection of proinsulin are described in Thrower et al., (2009), *Clinical and Experimental Immunology*, 155: 156-65 and in Liu et al., (2013) *Practical Diabetes*, 30: 148-50a, the entire contents of which are hereby incorporated in their entirety by reference. An example of an injectable formulation of proinsulin is Proinsulin peptide C19-A3 (GSLQPLA-LEGSLQKRGIV (SEQ ID NO: 2)) which can be obtained from Calbiochem-Novabiochem AG Clinalfa, affiliate of Merck Pharmaceuticals (Läufelfingen, Switzerland).

It will be understood, that the specific dose level for any particular patient will depend upon a variety of factors including the activity of the specific compound employed, the age, body weight, general health, sex, diet, time of administration, route of administration, and rate of excretion, drug combination (i.e. other drugs being used to treat the patient), and the stage of T1D (for example, pre-stage 1, stage 1, 2 or 3).

The present invention also contemplates the provision of pancreatic autoantigens, including proinsulin and IGRP indirectly, for example, by way of genetically modified bacteria, expressing proinsulin, derivatives or variants thereof. Examples of such bacteria are described for example in WO 2017/122180, the entire contents of which are herein incorporated in their entirety. More particularly, the present invention contemplates the provision of proinsulin or other pancreatic autoantigen to an individual, by administering to the individual a modified *Lactococcus lactis* strain, expressing and secreting proinsulin. The bacteria may be administered orally, e.g., in the form of an enterically coated pharmaceutical formulation which transports the bacteria to the gastrointestinal tract, e.g., to the lower part of the gastrointestinal tract (e.g., distal parts of the colon), where they will secrete a suitable dose of proinsulin.

Still further, the present invention contemplates the use of a plasmid-encoded proinsulin or other pancreatic autoantigen for administration to an individual requiring treatment. An example of such a plasmid construct, and methods for administration by intramuscular injection is described in Roep, et al., (2013) *Sci Transl Med*, 5: 191ra82, the entire contents of which are hereby incorporated by reference in their entirety.

It will be appreciated that in accordance with the methods of the present invention, the proinsulin (or derivative or variant thereof) and the inhibitor of proinflammatory cytokine-regulated gene expression may be administered concomitantly (i.e., during the same therapeutic window), or sequentially (i.e., during different therapeutic windows).

Preferably, the pancreatic autoantigen, derivative or variant thereof is administered in a non-inflammatory context.

As such, in one embodiment of the present invention, an individual identified as being at risk or displaying early signs and symptoms of T1D will undergo treatment with an anti-inflammatory compound (for example a JAK inhibitor), for a period of time before receiving pancreatic autoantigen. For example, in certain embodiments of the present invention, the individual will receive treatment with an anti-inflammatory agent for such time as there is a reduction in overt clinical indicators of inflammation (including, for example, as determined by determining levels of cytokine-induced phosphorylation of STAT proteins in samples of peripheral blood mononucleocytes (PBMCs) from the individual and indicators of islet inflammation).

In other words, the individual may receive treatment with a JAK inhibitor for a period sufficient to reduce cytokine signalling and other signs and symptoms of inflammation prior to administration of pancreatic autoantigen (or derivative or variant thereof). Accordingly, during a "first treatment phase", the individual will receive a therapeutically effective amount of an inhibitor of proinflammatory cytokine-regulated gene expression.

In any embodiment of the present invention, the individual will receive treatment with an anti-inflammatory compound, including a JAK inhibitor for between 1 to 12 weeks prior to receiving pancreatic autoantigen-specific immunotherapy. Preferably, the individual will receive treatment with an anti-inflammatory compound, including a JAK inhibitor for between 2 to 8 weeks prior to receiving pancreatic autoantigen-specific immunotherapy. More preferably, the individual will receive treatment with an anti-inflammatory compound, including a JAK inhibitor for 4 to 6 weeks prior to receiving pancreatic autoantigen-specific immunotherapy.

Following completion of the first phase of treatment, being the anti-inflammatory treatment, the individual may continue to receive treatment with the anti-inflammatory compound at the same time as treatment with the pancreatic autoantigen-specific immunotherapy. In other words, during the second phase of treatment, the individual may receive both a JAK inhibitor and proinsulin, or derivative or variant thereof. If the individual continues to receive anti-inflammatory treatment during the second phase of treatment, the dosing and/or frequency of administration compared with the first phase may be altered.

In certain embodiments, the anti-inflammatory compound is administered for at least 1 month before commencing administration of pancreatic autoantigen, derivative or variant thereof. Typically, the pancreatic autoantigen or a derivative or variant thereof is administered for at least 1 month, either alone or concomitantly with anti-inflammatory treatment.

Where the anti-inflammatory compound and the pancreatic autoantigen, derivative and variant thereof are administered concomitantly, dosing may occur simultaneously, or sequentially.

The present invention also provides a method of preventing or delaying the progression of T1D in an individual, comprising administering to an individual having, or suspected of having early signs of T1D, an anti-inflammatory compound, wherein preferably the anti-inflammatory compound inhibits or reduces the level of proinflammatory cytokine-mediated gene expression. More preferably, the anti-inflammatory compound is a JAK inhibitor.

In this scenario, the individual having or suspected of having early signs of T1D is able to produce endogenous pancreatic autoantigen (for example, proinsulin or other pancreatic autoantigen). Accordingly, the provision of exogenous anti-inflammatory compound, coupled with the endogenous pancreatic autoantigen enables the prevention of the progression of T1D in the individual, or delays or inhibits the progression of T1D in the individual. Examples of early signs of T1D are as described herein, including the development of autoantibodies against one or more pancreatic autoantigens, reduced levels of endogenous insulin production or evidence of pancreatic infiltration by immune cells.

The term 'administered' means administration of a therapeutically effective dose of the aforementioned pancreatic autoantigen (e.g. proinsulin), derivative or variant thereof and an anti-inflammatory compound. By 'therapeutically effective amount' is meant a dose that produces the effects for which it is administered. The exact dose will depend on the purpose of the treatment, and will be ascertainable by one skilled in the art using known techniques. As is known in the art and described above, adjustments for systemic versus localized delivery, age, body weight, general health, sex, diet, time of administration, drug interaction and the severity of the condition may be necessary, and will be ascertainable with routine experimentation by those skilled in the art.

The immune status generally, and specifically levels of regulatory T cells and cytokine profiles, may be readily determined throughout any treatment regime using conventional methods known to those skilled in the art. For example, regulatory T cell levels may be monitored by cytometric analysis following labelling with commercially available antibodies specific to T cell subsets. Other examples of methods suitable for determining the status of the subject include purification of peripheral blood mononuclear cells by density centrifugation followed by stimulation by incubation with well-known antigens such GAD, IA-2 family members, insulin or proinsulin. Resulting proliferation may be quantified by assaying for incorporation of $H^3$ thymidine. Said cytokines can be detected using, for example, specific cytokine antibodies. 24 hours after stimulation with antigen, stimulated cells can be phenotypically characterised by, for example, flow cytometric analysis of activation marker expression (for example CD69, CD44, CTLA4, CD25). Following cell surface labelling of activated cells, said cells may be further fixed and incubated with fluorochrome labelled antibodies to specific cytokines to determine intracellular cytokine levels. In particular, for example, cells may be further assessed by double labelling assays. The double labelled cells may be analysed utilising flow cytometric analysis or fluorescence spectroscopy.

Immune tolerance to insulin or other pancreatic autoantigen as an indicator of the success of the methods of the present invention, may be determined by conventional assays as herein described, for example by determining levels of insulin in samples obtained from the individual. Other means for determining the success of treatment (and provision of immunotolerance to insulin) include determining the frequency of autoantibodies to any pancreatic autoantigen described herein. In addition, the frequency of CD4+ T-cells or CD8+ T-cells in peripheral lymphoid tissue of the individual may be determined (whereby a decline in antigen-experienced specific CD4+ and/or CD8+ T cells is indicative of the development of immune tolerance to a particular pancreatic autoantigen, including immune tolerance to (pro)insulin, IGRP and other pancreatic autoantigens). The skilled person will be familiar with such methods, including as described in Jhala et al., (2016) *JCI Insight*, 1: e86065.

The present invention also includes a kit or "article of manufacture" which may comprise a container and a label or package insert on or associated with the container. Suitable containers include, for example, bottles, vials, syringes, blister pack, etc. The containers may be formed from a variety of materials such as glass or plastic. The container holds a therapeutic composition which is effective for treating the condition and may have a sterile access port (for example the container may be an intravenous solution bag or a vial having a stopper pierceable by a hypodermic injection needle). The label or package insert indicates that the therapeutic composition is used for treating the condition of choice. In one embodiment, the label or package insert includes instructions for use.

The kit may comprise (a) the anti-inflammatory compound and (b) proinsulin, derivative or variant thereof, or a pharmaceutical composition as described herein comprising proinsulin, derivative or variant thereof. The kit in this embodiment of the invention may further comprise a package insert indicating the composition and other active principle can be used to treat or prevent a disorder described herein. Alternatively, or additionally, the kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain embodiments a therapeutic composition as described herein may be provided in the form of a device, disposable or reusable, including a receptacle for holding the therapeutic, prophylactic or pharmaceutical composition. In one embodiment, the device is a syringe. The device may hold 1-2 mL of the therapeutic composition. The therapeutic or prophylactic composition may be provided in the device in a state that is ready for use or in a state requiring mixing or addition of further components.

It will be understood that the invention disclosed and defined in this specification extends to all alternative combinations of two or more of the individual features mentioned or evident from the text or drawings. All of these different combinations constitute various alternative aspects of the invention.

It will be understood that these examples are intended to demonstrate these and other aspects of the invention and although the examples describe certain embodiments of the invention, it will be understood that the examples do not limit these embodiments to these things. Various changes can be made and equivalents can be substituted and modifications made without departing from the aspects and/or principles of the invention mentioned above. All such changes, equivalents and modifications are intended to be within the scope of the claims set forth herein.

EXAMPLES

Example 1

Materials and Methods
Mice

All mice were bred and maintained at St Vincent's Institute. Mouse litters were administered their respective treatments (doxycycline and/or ruxolitinib) at the appropriate ages described below, prior to determination of their genotype. Genotyping of mice by PCR occurred after weaning, following which they were assigned to their appropriate cohorts according to genotype and treatment (FIG. 1A). Experiments were conducted in accordance with accepted standards of humane animal care, and were approved by the St Vincent's Hospital Animal Ethics Committee (Melbourne, Australia).

TIP Mice

Generation of tet-off TIP2 mice has been previously described in Jhala et al., (2016) *JCI Insight:* 1: e86065. Only progeny carrying both tetO-Ins2 and IEα-tTA transgenes were classed as TIP2 mice, and mice with a single transgene were used as controls. To turn off proinsulin expression, all TIP2 mice received doxycycline (10 mg/L) via mothers' drinking water from embryonic day 12 (transplacentally) to day 7 post-birth (translactationally) unless otherwise specified (FIG. 1A).

JAK1/JAK2 Inhibitor

The JAK1/JAK2 inhibitor ruxolitinib was purchased from Chemietek (USA). It was dissolved in a vehicle comprising 5% dimethyl acetamide, 0.25% phosphoric acid and 0.5% methyl cellulose. Mice receiving JAK inhibitor were treated with 80 mg/kg ruxolitinib daily by oral gavage from 2 to 4 weeks of age. Control mice received the same volume of vehicle by oral gavage.

Islet Isolation

Islets of Langherans were isolated using collagenase P (Roche) and Histopaque-1077 density gradients (Sigma-Aldrich) as previously described (Graham et al., (2016) Bio-protocol, 6: e1840).

Stimulation of Peripheral Blood and Western Blotting

Peripheral whole blood was stimulated with 100 U/mL IFN-γ (Biolegend) for 30 min at 37° C. Red blood cells were lysed (155 mmol/L NH$_4$Cl, 10 mmol/L Tris-HCl, pH 7.5). Samples were further treated with radioimmunoprecipitation assay buffer (R0278, Sigma), sample buffer (10% SDS, 30% glycerol, 0.02% bromophenol blue in 250 mM Tris-HCl, pH 6.8) and β-mercaptoethanol. Near-infrared fluorescent western blotting was performed using anti-p-STAT1 antibody (BD Biosciences), normalized to β-actin (Santa Cruz Biotechnology) and scanned on an Odyssey CLx imager.

Real-Time PCR Analysis

Total RNA was extracted using Isolate II RNA Mini kits (Bioline) from homogenized, snap-frozen spleen, thymus or from isolated islets. 1500 ng of purified RNA was used to synthesise first-strand cDNA in 20 μL of reaction volume using High Capacity cDNA Reverse Transcription kits (Applied Biosystem). Resulting cDNA was diluted 1:20 in nuclease-free water, from which 10 μL was analysed by real-time PCR using TaqMan gene expression assays (Applied Biosystem) and a Roche LightCycler 480. Primers for β-actin (Actb, housekeeping gene), murine preproinsulin 2 (Ins2), IFN-induced genes (Isg15, Ifit1, Oas1a, Oas1b), chemokine Cxcl10 and T cell marker Cd3e were used. Target gene expression was expressed relative to β-actin expression in each test sample using the formula $2^{-\Delta CT}$ where $\Delta CT=$Average $C_{T,\ target\ gene}$–Average $C_{T,\ actin}$ Diabetes Incidence The incidence of spontaneous diabetes in NOD mice is higher in females compared to males. Hence, female mice were monitored weekly for diabetes by measurement of urinary glucose levels using Diastix (Bayer). Those suspected of hyperglycaemia had further blood glucose level testing on two consecutive days using ACCU-CHEK Advantage II strips (Roche). Mice with two consecutive blood glucose measurements of greater than or equal to 15 mM were considered diabetic.

Histological Analysis of Insulitis

Pancreata were harvested, fixed in Bouin's fixative and embedded in paraffin. 5 μm sections were cut at 3 levels, each 150 μm apart, and stained with haematoxylin and eosin. Inflammation in islets was scored from 0 to 4 while blinded to treatment group: 0 (no inflammation), 1 (peri-islet infiltration involving <50% of circumference), 2 (peri-islet infiltration involving ≥50% of circumference and/or intraislet infiltrate), 3 (50-75% islet destruction), 4 (>75% islet destruction). Scoring was confirmed by a second blinded researcher. The insulitis score was calculated by [(0×number of grade 0 islets)+(0.25×number of grade-1 islets)+(0.5× number of grade-2 islets)+(0.75×number of grade-3 islets)+ (1×number grade-4 islets)]/total number of islets.

Tetramer and Magnetic Bead-Based Enrichment

Tetramer and magnetic bead-based enrichment was as previously described (20). Single-cell suspensions ($10^7$ cells) from peripheral lymphoid organs (spleen; inguinal and mesenteric lymph nodes) were stained with phycoerythrin (PE)-conjugated I-A ($g^7$)-INS$_{B10-23}$ (HLVERLYLVCGGEG (SEQ ID NO: 1)) tetramer for one hour at room temperature (obtained from NIH tetramer core). Cells were washed then stained with anti-PE MicroBeads (Miltenyi Biotec) and magnetically separated using an AutoMACSpro (Miltenyi Biotec).

Flow Cytometry

Fluorescent-labeled monoclonal antibodies specific for CD4 (GK1.5) bound to APC-Cy7, CD8 (53-6.7) bound to FITC, CD3 (500A2) bound to AmCyan, CD44 (IM7) bound to Alexa Fluor 700, and CD11 b (M1/70), CD11c (N418) and Ly6G (RB6-8C5) bound to Pacific Blue were used to stain magnetically sorted cells. Analysis was performed using FACSFortessa (BD Bioscience) and FlowJo software (TreeStar). Single cells were gated on forward and side scatter, and dead cells excluded using propidium iodide. CD11 b$^-$ CD11c$^-$ Ly6G$^-$ CD3$^+$ CD4$^+$ cells were gated as the target population for analysis of insulin tetramer-positive T cells.

IAA Assay

Insulin autoantibody (IAA) assays were noncompetitive assays performed with 96-well ELISA plates as previously described (21). Streptavidin-horseradish peroxidase (BioLegend) was used instead of streptavidin-Europium, followed by TMB substrate solution (BioLegend). Absorbance was measured at 450 nm using a Polarstar (BMG Labtech) microplate reader. True absorbance for each sample was calculated by subtracting absorbance of the sample in the absence of plate-bound insulin from absorbance of the sample in the presence of plate-bound insulin.

Statistics

Statistical analysis was performed using GraphPad Prism 7 software. Data were analysed using one or two-way ANOVA with Tukey's multiple comparison test, or two-tailed unpaired t test as indicated. Diabetes incidence curves were compared using log-rank analysis. All error bars are represented as mean±SEM. P values less than 0.05 were considered statistically significant.

Results

Expression of Thymic Proinsulin in TIP2 Mice is Doxycycline-Dependent

To confirm the use of tet-off TIP2 mice as a model for inducing proinsulin-specific tolerance, expression of proinsulin in thymic antigen presenting cells was measured using real time PCR at 11 days, 3 weeks and 5 weeks of age in both NOD and TIP2 mice. Doxycycline treatment was ceased at 7 days of age. At 11 days of age, thymic proinsulin expression in TIP2 mice remained suppressed (FIG. 1B). Within 2 weeks of doxycycline withdrawal, re-expression of thymic proinsulin in TIP2 mice aged 3 to 5 weeks was observed, while expression in NOD mice remained at baseline. However, expression had not yet reached levels found in TIP2 mice which never receive doxycycline, i.e., those that continuously express transgenic proinsulin. This suggests that whilst proinsulin expression in TIP2 mice is re-inducible within 2 weeks of doxycycline cessation, recovery of maximal expression is ongoing.

Ruxolitinib (JAK1/JAK2 Inhibitor) Blocks JAK/STAT Signalling in Peripheral Blood and Islets At 4 weeks of age, two hours after the last oral gavage of 80 mg/kg ruxolitinib or vehicle, peripheral blood and islets were harvested from NOD mice. Peripheral blood was stimulated with IFN-γ to induce phosphorylation of STAT1, integral in the JAK/STAT pathway downstream of IFN receptor activation. Treatment with ruxolitinib reduced STAT1 phosphorylation by greater than 50% compared to vehicle-treated NOD mice ($p=0.01$, two-tailed unpaired t test) (FIG. 2A), indicating inhibition of the JAK/STAT signalling pathway by ruxolitinib.

Islets were isolated and analysed for the expression of type I IFN-induced genes Isg15, Oas1a, Oas1b, Ifit1 and Mx1, as well as the IFNγ-inducible chemokine Cxcl10 and the T cell marker Cd3e. Expression of all IFN-induced genes bar Mx1 was significantly reduced in ruxolitinib-treated NOD islets. No difference in Cxcl10 or Cd3e mRNA expression was observed (FIG. 2B). Interestingly, expression of Cd3e in both vehicle and ruxolitinib cohorts was almost negligible, suggesting minimal T cell infiltration into pancreatic islets of NOD mice at 4 weeks of age. The lack of Cxcl10 upregulation is consistent with the absence of IFNγ-producing T cells. Collectively, these results are consistent with JAK inhibition downstream of type I IFN-induced signalling.

Short-Term Combination Therapy with JAK1/JAK2 Inhibitor and Proinsulin-Specific Immunotherapy in Early Life Prevents or Delays Diabetes Onset TIP2 mice were administered doxycycline transplacentally and translactationally from embryonic day 12 to day 7 post-birth via the mother's drinking water (10 mg/L) to suppress proinsulin expression. From 2 to 4 weeks of age while expression of proinsulin was recovering, TIP2 mice received 80 mg/kg of ruxolitinib (combination therapy; cohort 4; FIG. 1A) or vehicle (proinsulin monotherapy; cohort 3) via daily oral gavage. A further cohort of NOD mice were administered ruxolitinib monotherapy over this two week period (cohort 2). At 24 weeks of age (168 days), mice receiving combination therapy were protected from diabetes. In contrast, non-transgenic mice receiving vehicle (cohort 1) or cohorts receiving monotherapy were not protected (FIG. 3A). Several mice in these cohorts developed diabetes as young as 15 weeks of age (105 days). However, log-rank (Mantel-Cox) analysis revealed no significant difference in diabetes onset or incidence among the groups.

Short-Term Combination Therapy in Early Life Reduces Insulitis

Protection from diabetes was also reflected by the degree of insulitis at 19 to 28 weeks of age. Pancreatic immune cell infiltration in mice administered monotherapy was observed to be similar to that of vehicle-treated non-transgenic mice. Meanwhile, mice receiving combination therapy demonstrated significantly reduced islet infiltration ($p=0.017$, one-way ANOVA with Tukey's multiple comparisons test), similar to TIP2 mice which never received doxycycline and thus were tolerant to proinsulin (cohort 5) (FIG. 3B). Of particular significance was the increase in percentage of islets completely free of inflammation (insulitis score 0) (p<0.0001, two-way ANOVA with Tukey's multiple comparisons test) (FIG. 3C). These results indicate that administration of ruxolitinib in addition to inducing proinsulin-specific tolerance reduces cellular infiltration of islets, thus limiting 13 cell destruction, and preventing or delaying T1D.

Insulin Autoantibody Levels Following Combination Therapy

Insulin autoantibodies (IAA) are a reliable biomarker of autoimmunity in both NOD mice and humans. Thus, to test immune responses against insulin, we measured IAAs in each of the five cohorts between 20 and 28 weeks of age. Non-transgenic mice receiving vehicle (cohort 1) demonstrated the greatest IAA response (data not shown). All other cohorts showed less IAA response. Mean IAA levels in both monotherapy cohorts were similarly low, and interestingly, less than in mice which continuously expressed doxycycline (cohort 5).

Frequency of Antigen-Experienced Insulin-Specific CD4+ T Cells in Peripheral Lymphoid Tissue Following Combination Therapy To further examine lymphocytic infiltration of islets and tolerance to proinsulin, we determined the frequency of insulin $B_{9-23}$-specific CD4+ T cells in peripheral lymphoid tissue using I-A ($g^7$) tetramer. Interestingly, these insulin-specific CD4+ T cells were present in all cohorts of mice (data not shown). The percentage of antigen-experienced (CD44hi) insulin $B_{9-23}$-specific CD4+ T cells was highest in non-transgenic mice treated with vehicle (cohort 1), and was reduced in all other cohorts. As expected, this subset population was lowest in TIP2 mice continuously expressing proinsulin, yet interestingly still detectable. Data from these experiments show specificity of the insulin-specific tetramer and lack of binding by the HEL tetramer. Thus, overall these results suggest a decline in the proportion of antigen-experienced insulin $B_{9-23}$-specific CD4+ T cells following treatment with ruxolitinib, proinsulin-specific immunotherapy or the combination of both, most likely due to insulin tolerance.

DISCUSSION AND CONCLUSION

The combination of short-term treatment with ruxolitinib and proinsulin-specific immunotherapy in early life has been shown herein to reduce insulitis in NOD mice, and to prevent T1D onset at 24 weeks of age.

Without wishing to be bound by theory, the inventors believe that by inhibiting the IFN gene signature and reducing T cell infiltration into the pancreas, JAK inhibitors like ruxolitinib extend the window of opportunity where proinsulin-specific tolerance is effective.

Short-term combination therapy in early life demonstrates promise in the prevention or delay of diabetes in NOD mice. These results provide rationale for future clinical translation.

Proinsulin-specific immunotherapy on a background of immunomodulation by JAK inhibitors is safe and effective, and these findings suggest that short-term treatment in early life is sufficient to prevent or delay T1D, while significantly reducing pancreatic immune cell infiltration.

Example 2: Short-Term Combination Therapy with JAK Inhibitor and Proinsulin-Specific Immunotherapy after Onset of Insulitis Prevents or Delays Diabetes Onset Materials and Methods
TIP Mice
Generation of tet-off TIP2 mice was as describe in Example 1. To turn off proinsulin expression, all TIP2 mice received doxycycline (10 mg/L) via mothers' drinking water from embryonic day 12 (transplacentally) until weaning (day 21 post-birth) (translactationally), after weaning the mice were administered doxycycline via drinking water till 8 weeks (56 days) of age. Removal of doxycycline allowed the maximal recovery of proinsulin expression by 12 weeks (84 days) of age.

JAK1/JAK2 Inhibitor

The JAK1/JAK2 inhibitor was dissolved in vehicle comprising 5% dimethyl acetamide, 0.25% phosphoric acid and 0.5% methyl cellulose. Mice receiving JAK inhibitor were treated with 10 mg/kg dose twice daily by oral gavage from 12 to 14 weeks (day 84-98) of age. Control mice received the same volume of vehicle by oral gavage.

Diabetes Incidence

Female mice were monitored for diabetes weekly by measurement of urinary glucose levels using Diastix (Bayer). Those suspected of hyperglycaemia had further blood glucose level testing on two consecutive days using ACCU-CHEK Advantage II strips (Roche). Mice with two consecutive blood glucose measurements of greater than or equal to 15 mM were considered diabetic.

Results

TIP2 mice were administered doxycycline until 8 weeks of age to suppress proinsulin expression. At 12 weeks of age TIP2 mice received JAK inhibitor (combination therapy; cohort 3; FIG. 4A) or vehicle (proinsulin monotherapy; cohort 2). At 30 weeks of age (210 days), TIP2 mice receiving combination therapy were significantly protected from diabetes (FIG. 4B, cohort 3). In contrast, control mice (receiving vehicle without proinsulin therapy) were not protected (FIG. 4B, cohort 1). Mice receiving proinsulin monotherapy had a slight delay in diabetes progression (FIG. 4B, cohort 2), however, log-rank (Mantel-Cox) analysis revealed no significant difference in diabetes incidence as compared to cohort 1.

Example 3: Analysis of IGRP-Specific Cells

In NOD mice, the response against IGRP is prominent and T cells specific for IGRP can be easily detected as they are more numerous than proinsulin-specific T cells (2). TII mice (tetracycline-inducible IGRP) that are analogous to the TIP2 mice described above were generated so the effect of combination therapy on the number of antigen-specific T cells could be assessed.

Materials and Methods

TII mice received doxycycline until 10-weeks of age. After doxycycline was removed, IGRP was expressed in antigen presenting cells of mice carrying both tetO-IGRP and IEα-tTA transgenes. Mice were treated with 10 mg/kg JAK inhibitor or vehicle between 13-15 w of age for 2 weeks. Mice were analysed at 2 weeks (harvest immediately after stopping JAK inhibitor), 4 weeks (harvest two weeks after stopping JAK inhibitor), and 6 weeks (harvest four weeks after stopping JAK inhibitor). Data is from 1-3 experiments per time point with 3-4 mice per group/experiment.

Tetramer and magnetic bead-based enrichment was as previously described (Chee et al., (2014). *J Immunol* 192: 572-580; and Moon, et al. (2009) Nat Protoc 4: 565-581). Single-cell suspensions ($10^7$ cells) from peripheral lymphoid organs (spleen; inguinal and mesenteric lymph nodes) were stained with phycoerythrin (PE)-conjugated H-2Kd-IGRP206-214 tetramer for one hour at room temperature. Cells were washed then stained with anti-PE MicroBeads (Miltenyi Biotec) and magnetically separated using an AutoMACSpro (Miltenyi Biotec).

Fluorescent-labelled monoclonal antibodies specific for CD4 (GK1.5) bound to APC-Cy7, CD8 (53-6.7) bound to FITC, CD3 (500A2) bound to AmCyan, CD44 (IM7) bound to Alexa Fluor 700, and CD11 b (M1/70), CD11c (N418) and Ly6G (RB6-8C5) bound to Pacific Blue were used to stain magnetically sorted cells. Analysis was performed using FACSFortessa (BD Bioscience) and FlowJo software (TreeStar). Single cells were gated on forward and side scatter, and dead cells excluded using propidium iodide. CD11 b$^-$ CD11c$^-$ Ly6G$^-$ CD3$^+$ CD8$^+$ cells were gated as the target population for analysis of IGRP tetramer-positive T cells.

Results
Combination Therapy Affects Antigen-Specific Memory T Cells.

When TII mice that were induced to express IGRP from 10 weeks of age were treated with JAK inhibitor for 2 weeks, there was a decrease in IGRP specific memory T cells in PLO and in islets (FIG. 5, left panel TII-Veh vs TII-JAKi). While these cells returned 2 weeks after cessation of treatment in NOD mice (FIG. 5, NOD-JAKi), their numbers remained low in TII mice with antigen expression (FIG. 5, TII-JAKi), indicating that the combination of antigen therapy and JAK inhibitors not only targets antigen-specific T cells, but the depletion of these cells remains after JAK inhibitor therapy stops.

DISCUSSION

These results show that antigen-specific cells are deleted by combination therapy of antigen-tolerance and JAK inhibitor, and these cells remain deleted long term. This results in significant protection from diabetes development. At 10 weeks of age (when antigen expression was induced), NOD mice have evidence of insulin autoantibodies and islet inflammation (insulitis), indicating that autoimmunity has already begun in these mice. Therapy was induced after the onset of autoimmunity, suggesting that combination therapy has the potential to prevent T1D in subjects with evidence of autoimmunity but no clinical signs of disease (stage 1 and 2 T1D). This is further to the results shown in Example 1 showing protection in mice treated with combination therapy before the onset of autoimmunity.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A method of delaying the onset of type 1 diabetes (T1D) in an individual having or at risk of having T1D, the method comprising providing in the individual:
   an anti-inflammatory compound; and
   a pancreatic autoantigen or a derivative or variant thereof;
   thereby delaying the onset of T1D in the individual;
   wherein the anti-inflammatory compound is Ruxolitinib, and wherein the pancreatic autoantigen is proinsulin or a derivative or variant thereof.

2. The method of claim 1, wherein the individual at risk of developing type 1 diabetes has 2 or more autoantibodies against β-cell specific antigens, optionally wherein the β-cell specific antigens are selected from the group consisting of: Carboxypeptidase H, Chromogranin A, Glutamate decarboxylase (GAD), Imogen-38, Proinsulin/Insulin, Insulinoma antigen-2 and 2β, and zinc transporter 8 (ZnT8).

3. The method of claim 1, wherein the individual has a high-risk HLA genotype, optionally wherein the high-risk HLA genotype is DQ2 homozygous, DQ8 homozygous, or DQ2/DQ8 heterozygous.

4. The method of claim 1, wherein the individual displays at least one symptom of T1D selected from the group consisting of: polyuria, polydipsia, weight loss, fatigue, and diabetic ketoacidosis (DKA).

5. The method of claim 1, wherein the T1D is early stage type 1 diabetes.

6. The method of claim 1, wherein
(i) the anti-inflammatory compound and pancreatic autoantigen or a derivative or variant thereof are provided simultaneously; or
(ii) the anti-inflammatory compound is provided prior to the pancreatic autoantigen or a derivative or variant thereof, optionally wherein the anti-inflammatory compound is continued to be provided during the time proinsulin or a derivative or variant thereof is provided.

7. The method of claim 1, wherein the pancreatic autoantigen or derivative or variant thereof is administered orally, by inhalation, subcutaneously, intravenously, intranasally, intramuscularly or intradermally.

8. The method of claim 1, wherein the pancreatic autoantigen is a derivative of proinsulin, wherein the derivative of proinsulin is insulin.

9. The method of claim 1, wherein the pancreatic autoantigen or derivative or variant thereof is expressed by a genetically modified bacterium that has been administered to the subject.

10. The method of claim 1, wherein the pancreatic autoantigen or a derivative or variant thereof is provided in the individual by administering to the individual a dendritic cell which has been modified to express the pancreatic autoantigen or derivative or variant thereof.

11. The method of claim 1, wherein the pancreatic autoantigen or a derivative or variant thereof is provided in the individual by administering to the individual, a composition comprising a nucleic acid construct for expressing the pancreatic autoantigen or derivative or variant thereof in the individual.

* * * * *

SEQUENCE LISTING

```
<160> NUMBER OF SEQ ID NOS: 2

<210> SEQ ID NO 1
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1

His Leu Val Glu Arg Leu Tyr Leu Val Cys Gly Gly Glu Gly
1               5                  10

<210> SEQ ID NO 2
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 2

Gly Ser Leu Gln Pro Leu Ala Leu Glu Gly Ser Leu Gln Lys Arg Gly
1               5                   10                  15

Ile Val
```